(12) United States Patent
Sheppard et al.

(10) Patent No.: US 6,197,930 B1
(45) Date of Patent: Mar. 6, 2001

(54) ADIPOCYTE-SPECIFIC PROTEIN HOMOLOGS

(75) Inventors: Paul O. Sheppard, Redmond; Jacqueline M. Humes, Seattle, both of WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/140,804

(22) Filed: Aug. 26, 1998

Related U.S. Application Data

(60) Provisional application No. 60/056,983, filed on Aug. 26, 1997.

(51) Int. Cl.[7] ....................................................... C07K 1/00
(52) U.S. Cl. ................................................. 530/350; 514/2
(58) Field of Search ................................ 530/350; 514/2; 536/23.5

(56) References Cited

FOREIGN PATENT DOCUMENTS

96/39429    12/1996    (WO) .

OTHER PUBLICATIONS

Maeda et al., *Biochem. Biophys. Res. Comm. 221*: 286–289, 1996.

Scherer et al., *J. Biol. Chem.* 270:26746–26749, 1995.

Sellar et al., *Biochem. J. 274*: 481–490, 1991.

Gieser and Swaroop, *Genomics 13*: 873–876, 1992.

Daniel, C. et al., Virology 202(540–549)1994.*

* cited by examiner

*Primary Examiner*—Elizabeth Kemmerer
*Assistant Examiner*—Michael Brannock
(74) *Attorney, Agent, or Firm*—Susan E. Lingenfelter

(57) ABSTRACT

The present invention relates to polynucleotide and polypeptide molecules for zsig39, a novel member of the family of proteins bearing a collagen-like domain and a globular domain. The polypeptides, and polynucleotides encoding them, are involved in dimerization or oligomerization and may be used in the study thereof. The present invention also includes antibodies to the zsig39 polypeptides.

3 Claims, 2 Drawing Sheets

```
zsig39       MRPLLVLLLLGLAAG--------------------------------- : 15
HUMUPST2_1   MLLLGAVLLLLALP---------------------------------- : 14
C1QA_HUMAN   MEGPRGWLVLCVLAISLA------------------------------ : 18
HP25_TAMAS   MPAQRGGALSMGAAGFWILVLSITSALA-------------------- : 28
HP27_TAMAS   MYEAGKRASFMGGAGIWILALSVLMHVVCS------------------ : 30
CERL_RAT     MPAPGRGPRGPLLSMPGRRGALREPADFGSSLGAALALLLLLLPACCPVK : 50 zsig39       ---------------------------------SPPLDDNKIPSLCP : 29
HUMUPST2_1   --GHDQ---------------ETTTQGP----------GVLLPLPKGACT : 37
C1QA_HUMAN   --SMVT---------------EDLCRAPD-------------GKKGEAGR : 38
HP25_TAMAS   --DSNNQGNSEPC----------------------------------- : 39
HP27_TAMAS   ----ETQGNPESC----------------------------------- : 39
CERL_RAT     A-QNDTEPIVLEGKC----LVVCDSSPSGDGAVTSSL------------ : 82 zsig39       GH-PGLPGTPGHHGSQGLPG-RDGRDGRDGAPGAPGEKGEGGRPGLPGPR : 77
HUMUPST2_1   GWMAGIPGHPGHNGAPGRDG-RDGTPGEKGEKGDPGLIGPKGDIGETGVP : 86
C1QA_HUMAN   PGRRGRPGLKGEQGEPGAPGIRTGIQGLKGDQGEPGPSGNPGKVGYPGPS : 88
HP25_TAMAS   --------------------------GPPGPPGPPGIPGFPGAPGAL : 60
HP27_TAMAS   --------------------------NVPGPQGPPGMRGPPGTPGKP : 60
CERL_RAT     ------------------------------------------------ : 82 zsig39       GDPGPRGEAGPAGPTGPAGE---CSVPPRSAFSAKRSESRVPPPSDAPLP : 124
HUMUPST2_1   GAEGPRGFPGIQGRKGEPGE--GAY-VYRSAFSVGLETYVTI--PNMPIR : 131
C1QA_HUMAN   GPLGARGIPGIKGTKGSPGN--IKD-QPRPAFSAIRRNPPMG---GNVVI : 132
HP25_TAMAS   GPPGPPGVPGIPGPQGPPGDVEKCSSRPKSAFAVKLSERPPE--PFQPIV : 108
HP27_TAMAS   GPPGWNGFPGLPGPPGPPGMTVNCHSKGTSAFAVKANELPPA--PSQPVI : 108
CERL_RAT     -----------GISVRSG----SAKVAFSATRSTNHEPSEMSNRTMTIY : 116 zsig39       FDRVLVNEQGHYDAVTGKFTCQVPGVYYFAVHA-TV---YRASLQF-DLV : 169
HUMUPST2_1   FTKIFYNQQNHYDGSTGKFHCNIPGLYYFAYHI-TV----YMKDVKVSLF : 176
C1QA_HUMAN   FDTVITNQEEPYQNHSGRFVCTVPGYYYFTFQV-LSQ--WEICLSIVSSS : 179
HP25_TAMAS   FKEALYNQEGHFNMATGEFSCVLPGVYNFGFDIRLFQ--SSVKIRLMRDG : 156
HP27_TAMAS   FKEALHDAQGHFDLATGVFTCPVPGLYQFGFHIEAVQ--RAVKVSLMRNG : 156
CERL_RAT     FDQVLVNIGNHFDLASSIFVAPRKGIYSFSFHVVKVYNRQTIQVSLMQNG : 166 zsig39       KNGESIASFFQFFGGWPKPASLSGGAMVRLEPEDQVWVQVGVG-DYIGIY : 218
HUMUPST2_1   KKDKAMLFTYDQYQENNVDQASG-SVLLHLEVGDQVWLQVYGEGERNGLY : 225
C1QA_HUMAN   RGQVRRSLGFCDTTNKGLFQVVSGGMVLQLQQGDQVWVEKDP--KKGHIY : 227
HP25_TAMAS   I-QVREK----EAQANDSYKHAMGSVIMALGKGDKVWLESKL--KGTESE : 199
HP27_TAMAS   T-QVMER----EAEAQDGYEHISGTAILQLGMEDRVWLENKL--SQTDLE : 199
CERL_RAT     Y-PVISA----FAGDQDVTREAASNGVLLL-MEREDKVHLKL--ERGNLM : 208 zsig39       A--SIKTDSTFSGFLVYSDWHSSPVFA ; 243
HUMUPST2_1   ADNDNDS--TFTGFLLYHDTN------ ; 244
C1QA_HUMAN   QGSEADS--VFSGFLIFPSA------- ; 245
HP25_TAMAS   KGI-THI--VFFGYLLYGK-------- ; 215
HP27_TAMAS   RGT-VQA--VFSGFLIHEN-------- ; 215
CERL_RAT     GGW-KYS--TFSGFLVFPL-------- ; 224
```

FIG. 1

|            | Zsig39 | HUMUPST_2 | C1QA_HUMAN | HP25_TAMAS | HP27_TAMAS | CERL_RAT |
|------------|--------|-----------|------------|------------|------------|----------|
| Zsig39     | 100    |           |            |            |            |          |
| HUMUPST2_1 | 40     | 100       |            |            |            |          |
| C1QA_HUMAN | 37     | 33        | 100        |            |            |          |
| HP25_TAMAS | 35     | 31        | 32         | 100        |            |          |
| HP27_TAMAS | 34     | 29        | 32         | 53         | 100        |          |
| CERL_RAT   | 32     | 25        | 24         | 27         | 33         | 100      |

FIG. 2

ADIPOCYTE-SPECIFIC PROTEIN HOMOLOGS

REFERENCE TO RELATED APPLICATIONS

This application is related to Provisional Application No. 60/056,983, filed on Aug. 26, 1997. Under 35 U.S.C. §119 (e) (1), this application claims benefit of said Provisional Application.

BACKGROUND OF THE INVENTION

Energy balance (involving energy metabolism, nutritional state, lipid storage and the like) is an important criteria for health. This energy homeostasis involves food intake and metabolism of carbohydrates and lipids to generate energy necessary for voluntary and involuntary functions. Metabolism of proteins can lead to energy generation, but preferably leads to muscle formation or repair. Among other consequences, a lack of energy homeostasis lead to over or under formation of adipose tissue.

Formation and storage of fat is insulin-modulated. For example, insulin stimulates the transport of glucose into cells, where it is metabolized into α-glycerophosphate which is used in the esterification of fatty acids to permit storage thereof as triglycerides. In addition, adipocytes (fat cells) express a specific transport protein that enhances the transfer of free fatty acids into adipocytes.

Adipocytes also secrete several proteins believed to modulate homeostatic control of glucose and lipid metabolism. These additional adipocyte-secreted proteins include adipsin, complement factors C3 and B, tumor necrosis factor α, the ob gene product and Acrp30. Evidence also exists suggesting the existence of an insulin-regulated secretory pathway in adipocytes. Scherer et al., *J. Biol. Chem.* 270 (45): 26746–9, 1995. Over or under secretion of these moieties, impacted in part by over or under formation of adipose tissue, can lead to pathological conditions associated directly or indirectly with obesity or anorexia.

Acrp30 is a 247 amino acid polypeptide that is expressed exclusively by adipocytes. The Acrp30 polypeptide is composed of a amino-terminal signal sequence, a 27 amino acid stretch of no known homology, 22 perfect Gly-Xaa-Pro or imperfect Gly-Xaa-Xaa collagen repeats and a carboxy terminal globular domain. See, Scherer et al. as described above and International Patent Application No. WO96/39429. Acrp30, an abundant human serum protein regulated by insulin, shares structural similarity, particularly in the carboxy-terminal globular domain, to complement factor C1q and to a summer serum protein of hibernating Siberian chipmunks (Hib27). Expression of Acrp30 is induced over 103-fold during adipocyte differentiation. Acrp30 is suggested for use in modulating energy balance and in identifying adipocytes in test samples.

Another secreted protein that appears to be exclusively produced in adipocytes is apM1, described, for example, in Maeda et al., *Biochem. Biophys. Res. Comm.* 221: 286–9, 1996. A 4517 bp clone had a 244 amino acid open reading frame and a long 3' untranslated region. The protein included a signal sequence, an amino-terminal non-collagenous sequence, 22 collagen repeats (Gly-XAA-Pro or Gly-Xaa-Xaa), and a carboxy-terminal region with homology to collagen X, collagen VIII and complement protein C1q.

Complement factor C1q consists of six copies of three related polypeptides (A, B and C chains), with each polypeptide being about 225 amino acids long with a near amino-terminal collagen domain and a carboxy-terminal globular region. Six triple helical regions are formed by the collagen domains of the six A, six B and six C chains, forming a central region and six stalks. A globular head portion is formed by association of the globular carboxy terminal domain of an A, a B and a C chain. C1q is therefore composed of six globular heads linked via six collagen-like stalks to a central fibril region. Sellar et al., *Biochem. J.* 274: 481–90, 1991. This configuration is often referred to as a bouquet of flowers. Acrp30 has a similar bouquet structure formed from a single type of polypeptide chain.

Molecules capable of modulating energy homeostasis are sought for the study of this phenomena and for the prevention or treatment of imbalances. Also, molecules capable of modulating adipocyte secretory pathways are also sought as indirect energy homeostasis modulators and as research reagents.

The present invention provides such polypeptides for these and other uses that should be apparent to those skilled in the art from the teachings herein.

SUMMARY OF THE INVENTION

Within one aspect of the invention is provided an isolated polypeptide comprising a sequence of amino acid residues that is at least 80% identical to SEQ ID NO:2, wherein the sequence comprises: beta strands corresponding to amino acid residues 105–109, 128–130, 136–139, 143–146, 164–171, 176–182, 187–200, 204–210 and 226–231 of SEQ ID NO:2, wherein the beta strands are separated by at least two amino acid residues; and a receptor binding domain comprising amino acid residues 111–135 and 170–174 of SEQ ID NO:2. Within one embodiment the polypeptide is at least 90% identical to SEQ ID NO:2. Within another embodiment the polypeptide comprises a collagen-like domain having at least 22 collagen repeats. Within another embodiment the polypeptide comprises residues 19–243 of SEQ ID NO:2. Within yet another embodiment the polypeptide is covalently linked amino terminally or carboxy terminally to a moiety selected from the group consisting of affinity tags, toxins, radionucleotides, enzymes and fluorophores.

Within another aspect is provided. an isolated polypeptide selected from the group consisting of: a) a polypeptide having a sequence of amino acid residues from amino acid residue 30 to amino acid residue 95 of SEQ ID NO:2; b) a polypeptide having a sequence of amino acid residues from amino acid residue 30 to aminc acid residue 96 of SEQ ID NO:2; and c) a polypeptide having a sequence of amino acid residues from amino acid residue 30 to 97 of SEQ ID NO:2; d) a polypeptide having a sequence of amino acid residues from amino acid residue 30 to amino acid residue 98 of SEQ ID NO:2; e) a polypept.ide having a sequence of amino acid residues from amino acid residue 98 to amino acid residue 243 of SEQ ID NO:2; f) a polypeptide having a sequence of amino acid residues from amino acid residue 99 to amino acid residue 243 of SEQ ID NO:2; g) a polypeptide having a sequence of amino acid residues from amino acid residue 30 to amino acid residue 243 of SEQ ID NO:2; and h) a polypeptide having a sequence of amino acid residues that is 90% identical in amino acid sequence to a), b), c), d), e), f), g) or h).

Within another aspect is provided a fusion protein consisting essentially of a first portion and a second portion joined by a peptide bond, the first portion comprising a polypeptide selected from the group consisting of: a) a polypeptide comprising a sequence of amino acid residues that is at least 80% identical to SEQ ID NO:2, wherein the sequence comprises: beta strands corresponding to amino acid residues 105–109, 128–130, 136–139, 143–146, 164–171, 176–182, 187–200, 204–210 and 226–231 of SEQ ID NO:2, wherein the beta strands are separated by at least two amino acid residues; and a receptor binding domain comprising amino acid residues 111–135 and 170–174 of SEQ ID NO:2; b) a polypeptide comprising a sequence of amino acid residues as shown in SEQ ID NO:2 from amino acid residue 16 to amino acid residue 243; c) a polypeptide comprising a sequence of amino acid residues as shown in SEQ ID NO:2 from amino acid residue 1 to amino acid residue 243; d) a portion of the zsig39 polypeptide as shown in SEQ ID NO:2 containing the collagen-like domain or a portion of the collagen-like domain capable of dimerization or oligomerization; e) a portion of the zsig39 polypeptide as shown in SEQ ID NO:2, containing the globular-like domain or the receptor binding portion of the globular-like domain; or f) a portion of the zsig39 polypeptide as shown in SEQ ID NO:2, including the collagen-like domain and the globular domain; and the second portion comprising another polypeptide. Within one embodiment the first portion is selected from the group consisting of: a) a polypeptide having the sequence of amino acid residue 30 to amino acid residue 95 of SEQ ID NO:2; b) a polypeptide having the sequence of amino acid residue 30 to amino acid residue 96 of SEQ ID NO:2; c) a polypeptide having the sequence of amino acid residue 30 to amino acid residue 97 of SEQ ID NO:2; d) a polypeptide having the sequence of amino acid residue 30 to amino acid residue 98 of SEQ ID NO:2; e) a polypeptide having the sequence of amino acid residue 30 to amino acid residue 243 of SEQ ID NO:2; f) a polypeptide having the sequence of amino acid residue 98 to amino acid residue 243 of SEQ ID NO:2; and g) a polypeptide having the sequence of amino acid residue 99 to amino acid residue 243 of SEQ ID NO:2.

Within another aspect is provided a fusion protein comprising a secretory signal sequence having the amino acid sequence of amino acid residues 1–15 or 1–18 of SEQ ID NO:2, wherein the secretory signal sequence is operably linked to an additional polypeptide.

Within yet another aspect is pharmaceutical composition comprising a polypeptide as described above, in combination with a pharmaceutically acceptable vehicle.

Also provided is an antibody that specifically binds to an epitope of a polypeptide as described above.

Further provided is an isolated polynucleotide encoding a polypeptide comprising a sequence of amino acid residues that is at least 80% identical to SEQ ID NO:2, wherein the sequence comprises: beta strands corresponding to amino acid residues 105–109, 128–130, 136–139, 143–146, 164–171, 176–182, 187–200, 204–210 and 226–231 of SEQ ID NO:2, wherein the beta strands are separated by at least two amino acid residues; and a receptor binding domain comprising amino acid residues 111–135 and 170–174 of SEQ ID NO:2. Within one embodiment the polypeptide is at least 90% identical to SEQ ID NO:2. Within another embodiment the polypeptide comprises a collagen-like domain having at least 22 collagen repeats. Within another embodiment the polynucleotide is DNA.

Within yet another aspect is provided an isolated polynucleotide selected from the group consisting of: a) a sequence of nucleotides from nucleotide 243 to nucleotide 962 of SEQ ID NO:1; b) a sequence of nucleotides from nucleotide 252 to nucleotide 962 of SEQ ID NO:1; c) a sequence of nucleotides from nucleotide 285 to nucleotide 482 of SEQ ID NO:1; d) a sequence of nucleotides from nucleotide 285 to nucleotide 485 of SEQ ID NO:1; e) a sequence of nucleotides from nucleotide 285 to nucleotide 488 of SEQ ID NO:1; f) a sequence of nucleotides from nucleotide 285 to nucleotide 491 of SEQ ID NO:1; g) a sequence of nucleotides from nucleotide 285 to nucleotide 926 of SEQ ID NO:1; h) a sequence of nucleotides from nucleotide 491 to nucleotide 926 of SEQ ID NO:1; i) a polynucleotide encoding a polypeptide having a sequence of nucleotides that is at least 30% identical in nucleotide sequence to a), b), c), d), e), f), g) and h); j) nucleotide sequences complementary to a), b), c), d), e), f), g), h) or i); and k) degenerate nucleotide sequences of a), b), c), d), e), f), g), h), i) or j).

Within another aspect is provided an isolated polynucleotide encoding a fusion protein consisting essentially of a first portion and a second portion joined by a peptide bond, the first portion is selected from the group consisting of: a) a polypeptide comprising a sequence of amino acid residues that is at least 80% identical to SEQ ID NO:2, wherein the sequence comprises: beta strands corresponding to amino acid residues 105–109, 128–130, 136–139, 143–146, 164–171, 176–182, 187–200, 204–210 and 226–231 of SEQ ID NO:2, wherein the beta strands are separated by at least two amino acid residues; and a receptor binding domain comprising amino acid residues 111–135 and 170–174 of SEQ ID NO:2; b) a polypeptide comprising a sequence of amino acid residues as shown in SEQ ID NO:2 from amino acid residue 16 to amino acid residue 243; c) a polypeptide comprising a sequence of amino acid residues as shown in SEQ ID NO:2 from amino acid residue 1 to amino acid residue 243; d) a portion of the zsig39 polypeptide as shown in SEQ ID NO:2 containing the collagen-like domain or a portion of the collagen-like domain capable of dimerization or oligomerization; e) a portion of the zsig39 polypeptide as shown in SEQ ID NO:2, containing the globular-like domain or an active portion of the globular-like domain; or f) a portion of the zsig39 polypeptide as shown in SEQ ID NO:2, including the collagen-like domain and the globular domain; and the second portion comprising another polypeptide.

Within another aspect is provided an isolated polynucleotide encoding a fusion protein comprising a secretory signal sequence having the amino acid sequence of amino acid residues 1–15 or 1–18 of SEQ ID NO:2, wherein the secretory signal sequence is operably linked to an additional polypeptide.

Within yet another aspect is an isolated polynucleotide comprising the sequence of nucleotide 1 to nucleotide 729 of SEQ ID NO:10.

Also provided is an expression vector comprising the following operably linked elements: a transcription promoter; a DNA segment encoding a polypeptide as described above; and a transcription terminator. Within one embodiment the DNA segment encodes a polypeptide that is at least 90% identical to SEQ ID NO:2. Within another embodiment the DNA segment encodes a polypeptide further comprising a collagen-like domain having at least 22 collagen repeats. Within yet another embodiment the DNA segment encodes a polypeptide covalently linked amino terminally or carboxy terminally to an affinity tag. Within still another embodiment the DNA segment further encodes a secretory signal sequence operably linked to the polypeptide. Within yet another embodiment the secretory signal sequence comprises residues 1–15 or 1–18 of SEQ ID NO:2.

Also provided is a cultured cell into which has been introduced an expression vector comprising the following operably linked elements: a transcription promoter; a DNA segment encoding a polypeptide as described above; and a transcription terminator; wherein the cell expresses the polypeptide encoded by the DNA segment.

Within another aspect is provided a method of producing a polypeptide comprising: culturing a cell into which has been introduced an expression vector comprising the following operably linked elements: a transcription promoter; a DNA segment encoding a polypeptide as described above; and a transcription terminator; whereby the cell expresses the polypeptide encoded by the DNA segment; and recovering the expressed polypeptide.

Within another aspect is an oligonucleotide probe or primer comprising at least 14 contiguous nucleotides of a polynucleotide of SEQ ID NO:10 or a sequence complementary to SEQ ID NO:10.

Within yet another aspect is a method for modulating free fatty acid metabolism by administering a pharmaceutically effective dose of a polypeptide as described above.

BRIEF DESCRIPTION OF THE DRAWINGS

FIG. 1 illustrates a multiple alignment of and zsig39 polypeptide of the present invention (SEQ ID NO:2) and HUMUPST2_1 (SEQ ID NO:3) (Maeda et al., *Biochem. Biophys. Res. Comm.* 221(2): 286–9, 1996); C1QA_HUMAN (SEQ ID NO:4) (Sellar et al., *Biochem. J.* 274: 481–90, 1991, Reid, *Biochem. J.* 179: 367–71, 1979, and Reid et al., *Biochem. J.* 203: 559–69, 1982); HP25_TAMAS (SEQ ID NO:5) (Takamatsu et al., *Mol. Cell. Biol.* 13: 1516–21, 1993 and Kondo & Kondo, *J. Biol. Chem.* 267: 473–8, 1992); HP27_TAMAS (SEQ ID NO:6) (Takamatsu et al. and Kondo & Kondo referenced above); and CERL_RAT (SEQ ID NO:7)(Wada & Ohtani, *Brain Ras. Mol. Brain Res.* 9: 71–7, 1991).

FIG. 2 is a matrix showing percent amino acid identity in a comparison of the six proteins shown in the multiple alignment FIG. 1.

DETAILED DESCRIPTION OF THE INVENTION

Prior to setting forth the invention in detail, it may be helpful to the understanding thereof to define the following terms.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), substance P, Flag™ peptide (Hopp et al., *Biotechnology* 6:1204–1210, 1988; available from Eastman Kodak Co., New Haven, Conn.), Glu-Glu affinity tag (Grussenmeyer et al., *Proc. Natl. Acad. Sci. USA* 82:7925–4, 1995), streptavidin binding peptide, or other antigenic epitope or binding domain. See, in general Ford et al., *Protein Expression and Purification* 2: 95–107, 1991. DNAs encoding affinity tags are available from commercial suppliers (e.g., Pharmacia Biotech, Piscataway, N.J.).

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a protein is located proximal to the carboxyl terminus of the reference sequence, but is not necessarily at the carboxyl terminus of the complete protein.

The term "collagen or collagen-like domain" refers to a series of repeating triplet amino acid sequences, "repeats" or "collagen repeats", Gly-Xaa-Pro or Gly-Xaa-Xaa, where Xaa is any amino acid residue. Such domains may contain as many as 22 collagen repeats or more. Fragments or proteins containing such collagen-like domains may form homomeric constructs (dimers or oligomers of the same fragment or protein). Moreover, such fragments or proteins containing such collagen-like domains may form heteromeric constructs (dimers or oligomers of different fragments or proteins).

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, denotes that the segments are arranged so that they function in concert for their intended purposes, e.g. transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

The term "promoter" denotes a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a polypeptide having homology to an adipocyte complement related protein (Acrp30). See, for example, Scherer et al., *J. Biol. Chem.* 270(45): 26746–9, 1995. The polypeptide Acrp30 is shown in SEQ ID NO:8. Acrp30 appears to be highly related to human apM1 (HUMUPST2_1 in FIGS. 1 and 2, SEQ ID NO:3), with the most significant differences observed in the secretory sequence.

The novel DNA sequence encodes a polypeptide having an amino-terminal signal sequence, an adjacent N-terminal region of non-homology, a truncated collagen domain composed of Gly-Xaa-Xaa or Gly-Xaa-Pro repeats and a carboxy-terminal globular portion. The novel polynucleotide sequence also contains a long 3' untranslated region. The general polypeptide structure set forth above is shared by Acrp30 (SEQ ID NO:8) and HUMUPST2_1 (SEQ ID NO:3). Also, the HUJMUPST2_1 DNA sequence (SEQ ID NO:9) is characterized by a long 3' untranslated region. Moreover, Acrp30 and all of the sequences aligned in FIG. 1, with the exception of CERL_RAT (SEQ ID NO:7), share a conserved cysteine residue at position 144 of the zsig39 polypeptide as shown in FIG. 1 and SEQ ID NO: 2. Other regions of homology, found in the carboxy-terminal globular portion in the aligned proteins, are identified herein as useful primers for searching for other family members. Acrp30, for example, would be identified in a search using the primers. Also, the zsig39 polypeptides of the present invention include a putative cell attachment site, the RGD motif at amino acid residues 77–79 of SEQ ID NO: 2. See, for example, Ruoslahti and Pierschbacher, *Cell* 44: 517–8, 1986 and d'Souza et al., *Trends Biochem. Sci.* 16: 246–50, 1991, for discussions of the RGD peptide motif and its role in adhesion.

Analysis of the tissue distribution of the mRNA corresponding to this novel DNA was conducted as described in Example 2 herein. One transcript size was observed at approximately 1.2 kb. Signal intensity was, highest for small intestine and heart, with relatively less intense signals in pancreas, skeletal muscle, kidney and thyroid, and with lower intensity signals in placenta, lung, liver, spleen, prostate, ovary, colon, stomach, spinal cord, lymph node, trachea, adrenal gland and bone marrow. The polypeptide has been designated zsig39 polypeptide. A Dot blot indicated expression of zsig39 polypeptide in the subthalamic nucleus, hippocampus, medulla oblongata and thalamus. A human gut blot showed expression in the human colorectal adenocarcinoma cell line SW480, small intestine tissue, stomach tissue, normal human colon cell line, FHC; and normal fetal small intestine cell line FHs74 Int.

The novel zsig39 polypeptides of the present invention were initially identified by querying an EST database for secretory signal sequences, characterized by an upstream methionine start site, a hydrophobic region of approximately 13 amino acids and a cleavage site, in an effort to select for secreted proteins. Polypeptides corresponding to ESTs meeting those search criteria were compared to known sequences to identify secreted proteins having homology to known ligands. A single EST sequence was discovered and predicted to be a secreted protein. The novel polypeptide encoded by the full length cDNA enable the identification of a homolog relationship with adipocyte complement related protein Acrp30 (SEQ ID NO:8) and adipocyte secreted protein apM1 (HUMUPST2_1 in FIGS. 1 and 2, SEQ ID NO:3). Somewhat more distant homology was also identified to complement component Clq A chain, two factors observed in the active state of hibernating Siberian woodchucks (HP25_TAMAS (SEQ ID NO:5) and HP27_TAMAS (SEQ ID NO:6)) and a rat brain protein (CERL_RAT, SEQ ID NO:7), as shown in FIGS. 1 and 2.

The full sequence of the zsig39 polypeptide was obtained from a single clone believed to contain it, wherein the clone was obtained from a lung tissue library. Other libraries that might also be searched for such clones include heart, small intestine, pancreas, skeletal muscle, kidney, thyroid, subthalamic nucleus, hippocampus, medulla oblongata, thalamus and the like.

The nucleotide sequence of the N-terminal EST is described in SEQ ID NO:1, and its deduced amino acid sequence is described in SEQ ID NO:2. As described generally above, the zsig39 polypeptide includes a signal sequence, ranging from amino acid 1 (Met) to amino acid residue 15 (Gly). An alternative signal sequence ranges from amino acid 1 (Met) to amino acid 18 (Pro). The mature polypeptide therefore ranges from amino acid 16 (Ser) or 19 (Leu) to amino acid 243 (Ala). Within the mature polypeptide, an N-terminal region of limited homology is found, ranging between amino acid residue 20 (Asp) and 29 (Pro), wherein the cysteine at position 28 may provide similar structure/function as the cysteine found at position 36 in HUMUPST2_1 and in the N-terminal region of HP25_TAMAS and HP27_TAMAS. In addition, a collagen domain is found between amino acid 30 (Gly) and 95 (Ala), 96 (Gly), 97 (Glu) or 98 (Cys). In the collagen domain, 9 perfect Gly-Xaa-Pro and 13 or 14 imperfect Gly-Xaa-Xaa repeats are observed. Acrp30 contains 22 perfect or imperfect repeats.

The zsig39 polypeptide also includes a carboxy-terminal globular domain, ranging from about amino acid 98 (Cys) or 99 (Ser) to 243 (Ala). The globular domain of ACRP30 has been determined to have a 10 beta strand "jelly roll" topology (Shapiro and Scherer, *Curr. Biol.* 8:335–8, 1998) and the zsig39 sequence as represented by SEQ ID NO:2 contains all 10 beta-strands of this structure (amino acid residues 105–109, 128–130, 136–139, 143–146, 164–171, 176–182, 187–200, 204–210 and 226–231 of SEQ ID NO:2). These strands have been designated "A", "A'", "B", "B'", "C'", "D'", "E'", "F'", "G" and "H" respectively. Also, two receptor binding loops, amino acid residues 111–139 and 170–182 of SEQ ID NO:2, are represented. The core receptor binding region is predicted to include amino acid residues 111–135 and 170–174 of SEQ ID NO:2. Those skilled in the art will recognize that these boundaries are approximate, and are based on alignments with known proteins and predictions of protein folding. Amino acid residues 149 (Glu), 151 (Tyr), 199 (Leu) and 227 (Phe) appear to be conserved across the superfamily including CD40, TNFα, ACRP30 and zsig39.

The proteins of the present invention comprise a sequence of amino acid residues that is at least 80% identical to SEQ ID NO:2. Within certain embodiments of the invention, the sequence is at least 90% or 95% identical to SEQ ID NO:2.

Another aspect of the present invention includes zsig39 polypeptide fragments. Preferred fragments include the collagen-like domain of zsig39 polypeptides, ranging from amino acid 30 (Gly) to amino acid 95 (Ala), 96 (Gly), 97 (Glu) or 98 (Cys) of SEQ ID NO:2, a portion of the zsig39 polypeptide containing the collagen-like domain or a portion of the collagen-like domain capable of dimerization or oligomerization. These fragments are particularly useful in the study of collagen dimerization or oligomerization or in formation of fusion proteins as described more fully below. Polynucleotides encoding such fragments are also encompassed by the present invention, including the group consisting of (a) polynucleotide molecules comprising a sequence of nucleotides as shown in SEQ ID NO: 1 from nucleotide 1, 198, 242, 251 or 285 to nucleotide 482, 485, 488 or 491; (b) polynucleotide molecules that encode a zsig39 polypeptide fragment that is at least 80% identical to the amino acid sequence of SEQ ID NO: 2 from amino acid residue 30 (Gly) to amino acid residue 96 (Gly), 97 (Glu), 98 (Cys); (c) molecules complementary to (a) or (b); and (f) degenerate nucleotide sequences encoding a zsig39 polypeptide collagen-like domain fragment.

Such fragments or proteins containing such collagen-like domains may form homomeric constructs (dimers or oligomers of the same fragment or protein). Moreover, such fragments or proteins containing such collagen-like domains may form heteromeric constructs (dimers or oligomers of different fragments or proteins) Other components of heteromeric constructs may include Acrp30 and other polypeptides characterized by collagen-like domains as are described herein or known in the art. These homomeric and heteromeric constructs are contemplated by the present invention.

Other preferred fragments include the globular domain of zsig39 polypeptides, ranging from amino acid 98(Cys) or 99 (Ser) to 243 (Ala) of SEQ ID NO:2, particularly from amino acid residue 105 to 231 of SEQ ID NO:2, a portion of the zsig39 polypeptide containing the globular-like domain or an active portion of the globular-like domain. These fragments are particularly useful in the study or modulation of energy balance or neurotransmission, particularly diet- or stress-related neurotransmission. Anti-microbial activity may also be present in such fragments. The globular domain of Acrp30 proteins have been shown to assemble as a multimer of trimers. The trimers can be homo or heteromeric (Shapiro and Scherer, *ibid.*). Such fragments would also be useful for studying multimerization and receptor binding of zsig39 and other related proteins such as Acrp30 and TNFα. Polynucleotides encoding such fragments are also encompassed by the present invention, including the group consisting of (a) polynucleotide molecules comprising a sequence of nucleotides as shown in SEQ ID NO:1 from nucleotide 489 or 492 to nucleotide 926 or 1347; (b) polynucleotide molecules that encode a zsig39 polypeptide fragment that is at least 80% identical to the amino acid sequence of SEQ ID NO:2 from amino acid residue 98 (Cys) or 99 (Ser) to amino acid residue 243 (Ala); (c) molecules complementary to (a) or (b); and (f) degenerate nucleotide sequences encoding a zsig39 polypeptide globular domain fragment.

Another zsig39 polypeptide fragment of the present invention include both the collagen-like domain and the globular domain ranging from amino acid residue 30 (Gly) to 243 (Ala) of SEQ ID NO:2. Polynucleotides encoding such fragments are also encompassed by the present invention, including the group consisting of (a) polynucleotide molecules comprising a sequence of nucleotides as shown in SEQ ID NO:1 from nucleotide 285 to nucleotide 926 or 1347; (b) polynucleotide molecules that encode a zsig39 polypeptide fragment that is at least 80% identical to the amino acid sequence of SEQ ID NO:2 from amino acid residue 30 (Gly) to amino acid residue 243 (Ala); (c) molecules complementary to (a) or (b); and (f) degenerate nucleotide sequences encoding a zsig39 polypeptide collagen-like domain-globular domain fragment.

Zsig39 fragments may be evaluated with respect to their anti-microbial properties according to procedures known in the art. See, for example, Barsum et al., *Eur. Respir. J.* 8(5): 709–14, 1995; Sandovsky-Losica et al., *J. Med. Vet. Mycol* (England) 28(4): 279–87, 1990; Mehentee et al., *J. Gen. Microbiol* (England) 135 (Pt. 8): 2181–8, 1989; Segal and Savage, *Journal of Medical and Veterinary Mycology* 24: 477–479, 1986 and the like. If desired, zsig39 polypeptide fragment performance in this regard can be compared to proteins known to be functional in this regard, such as proline-rich proteins, lysozyme, histatins, lactoperoxidase or the like. In addition, zsig39 polypeptide fragments may be evaluated in combination with one or more anti-microbial agents to identify synergistic effects. One of ordinary skill in the art will recognize that the anti-microbial properties of zsig39 polypeptides, fusion proteins, agonists, antagonists and antibodies may be similarly evaluated.

As neurotransmitters or neurotransmission modulators, zsig39 polypeptide fragments as well as zsig39 polypeptides, fusion proteins, agonists, antagonists or antibodies of the present invention may also modulate calcium ion concentration, muscle contraction, hormone secretion, DNA synthesis or cell growth, inositol phosphate turnover, arachidonate release, phospholipase-C activation, gastric emptying, human neutrophil activation or ADCC capability, superoxide anion production and the like. Evaluation of these properties can be conducted by known methods, such as those set forth herein.

The impact of zsig39 polypeptide, fragment, fusion, agonist or antagonist on intracellular calcium level may be assessed by methods known in the art, such as those described by Dobrzanski et al., *Reqlatory Peptides* 45: 341–52, 1993, and the like. The impact of zsig39 polypeptide, fragment, fusion, agonist or antagonist on muscle contraction may be assessed by methods known in the art, such as those described by Smits & Lebebvre, *J. Auton. Pharmacol.* 14: 383–92, 1994, Belloli et al., *J. Vet. Pharmacol. Therap.* 17: 379–83, 1994, Maggi et al., *Regulatory Peptides* 53: 259–74, 1994, and the like. The impact of zsig39 polypeptide, fragment, fusion, agonist or antagonist on hormone secretion may be assessed by methods known in the art, such as those for prolactin release described by Henriksen et al., *J. of Receptor & Signal Transduction Research* 15(1–4): 529–41, 1995, and the like.

The impact of zsig39 polypeptide, fragment, fusion, agonist or antagonist on DNA synthesis or cell growth may be assessed by methods known in the art, such as those described by Dobrzanski et al., *Regulatory Peptides* 45: 341–52, 1993, and the like. The impact of zsig39 polypeptide, fragment, fusion, agonist or antagonist on inositol phosphate turnover may be assessed by methods known in the art, such as those described by Dobrzanski et al., *Regulatory Peptides* 45: 341–52, 1993, and the like.

Also, the impact of zsig39 polypeptide, fragment, fusion, agonist or antagonist on arachidonate release may be assessed by methods known in the art, such as those described by Dobrzanski et al., *Regulatory Peptides* 45: 341–52, 1993, and the like. The impact of zsig39 polypeptide, fragment, fusion, agonist or antagonist on phospholipase-C activation may be assessed by methods known in the art, such as those described by Dobrzanski et al., *Regulatory Peptides* 45: 341–52, 1993, and the like. The impact of zsig39 polypeptide, fragment, fusion, agonist or antagonist on gastric emptying may be assessed by methods known in the art, such as those described by Varga et al., *Eur. J. Pharmacol.* 286: 109–112, 1995, and the like. The impact of zsig39 polypeptide, fragment, fusion, agonist or antagonist on human neutrophil activation and ADCC capability may be assessed by methods known in the art, such as those described by Wozniak et al., *Immunology* 78: 629–34, 1993, and the like. The impact of zsig39 polypeptide, fragment, fusion, agonist or antagonist on superoxide anion production may be assessed by methods known in the art, such as those described by Wozniak et al., *Immunology* 78: 629–34, 1993, and the like.

The present invention also provides zsig39 fusion proteins. For example, fusion proteins of the present invention encompass (1) a polypeptide selected from the following: a) a polypeptide comprising a sequence of amino acid residues that is at least 80% identical in amino acid sequence to amino acid residue 19 to amino acid residue 243 of SEQ ID NO:2; b) a polypeptide comprising a sequence of amino acid residues as shown in SEQ ID NO:2 from amino acid residue 16 to amino acid residue 243; c) a polypeptide comprising a sequence of amino acid residues as shown in SEQ ID NO:2 from amino acid residue 1 to amino acid residue 243; d) a portion of the zsig39 polypeptide as shown in SEQ ID NO:2 containing the collagen-like domain or a portion of the collagen-like domain capable of dimerization or oligomerization; e) a portion of the zsig39 polypeptide as shown in SEQ ID NO:2, containing the globular-like domain or an active portion of the globular-like domain; or f) a portion of the zsig39 polypeptide as shown in SEQ ID NO:2, including the collagen-like domain and the globular domain; and (2) another polypeptide. The other polypeptide may be alternative cr additional globular domain, an alternative or additional collagen-like domain, a signal peptide to facilitate secretion of the fusion protein or the like. The globular domain of complement bind IgG, thus, the globular domain of zsig39 polypeptide, fragment or fusion may have a similar role.

Zsig39 polypeptides, ranging from amino acid 1 (Met) to amino acid 243 (Ala); the alternative mature zsig39 polypeptides, ranging from amino acid 16 (Ser) or amino acid 19 (Leu) to amino acid 243 (Ala); or the alternative secretion leader fragments thereof, which fragments range from amino acid 1 (Met) to amino acid 15 (Gly) or amino acid 18 (Pro) may be used in the study of secretion of proteins from cells. In preferred embodiments of this aspect of the present invention, the mature polypeptides are formed as fusion proteins with putative secretory signal sequences; plasmids bearing regulatory regions capable of directing the expression of the fusion protein is introduced into test cells; and secretion of mature protein is monitored. In other preferred embodiments of this aspect of the present invention, the alternative secretion leader fragments are formed as fusion proteins with alternative proteins selected for secretion; plasmids bearing regulatory regions capable of directing the expression of the fusion protein are introduced into test cells; and secretion of the protein is monitored. The monitoring may be done by techniques known in the art, such as HPLC and the like.

The highly conserved amino acids, particularly those in the carboxy-terminal globular domain of zsig39 polypeptide, can be used as a tool to identify new family members. For instance, reverse transcripton-polymerase chain reaction (RT-PCR) can be used to amplify sequences encoding the conserved motifs from RNA obtained from a variety of tissue sources. In particular, highly degenerate primers designed from conserved sequences are useful for this purpose. In particular, the following primers are useful for this purpose:

1) Amino acids 121–126 of SEQ ID NO: 2 (corresponding to nucleotides 558–575 of SEQ ID NO: 1);
2) Amino acids 131–136 of SEQ ID NO: 2 (corresponding to nucleotides 588–605 of SEQ ID NO: 1);
3) Amino acids 149–154 of SEQ ID NO: 2 (corresponding to nucleotides 642–659 of SEQ ID NO: 1);
4) Amino acids 202–207 of SEQ ID NO: 2 (corresponding to nucleotides 801–818 of SEQ ID NO: 1); and
5) Amino acids 226–231 of SEQ ID NO: 2 (corresponding to nucleotides 873–890 of SEQ ID NO: 1).

The present invention also contemplates degenerate probes based upon the polynucleotides described above. Probes corresponding to complements of the polynucleotides set forth above are also encompassed.

Within preferred embodiments of the invention the isolated polynucleotides will hybridize to similar sized regions of SEQ ID NO: 2, SEQ ID NO: 7, SEQ ID NO: 8, SEQ ID NO: 9, other probes specifically recited herein or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

Those skilled in the art will readily recognize that, in view of the degeneracy of the genetic code, considerable sequence variation is possible among these polynucleotide molecules. SEQ ID NO:10 is a degenerate polynucleotide sequence that encompasses all polynucleotides that could encode the zsig39 polypeptide of SEQ ID NO:2 (amino acids 1–243). Those skilled in the art will also recognize that the degenerate sequence of SEQ ID NO:10 also provides all RNA sequences encoding SEQ ID NO:2 by substituting U for T. Thus, zsig39 polypeptide-encoding polynucleotides ranging from nucleotide 1, 46 or 55 to nucleotide 729 of SEQ ID NO:10 are contemplated by the present invention. Also contemplated by the present invention are fragments and fusions as described above with respect to SEQ ID NO:1, which are formed from analogous regions of SEQ ID NO:10, wherein nucleotides 198 to 926 of SEQ ID NO):1 correspond to nucleotides 1 to 729 of SEQ ID NO:10. The symbols in SEQ ID NO:10 are summarized in Table 1 below.

TABLE 1

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | W | A\|T |
| W | A\|T | S | C\|G |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:10, encompassing all possible codons for a given amino acid, are set forth in Table 2 below.

TABLE 2

| Amino Acid | Letter | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | CAN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |
| Gap | - | - | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may have some incorrect amino acids, but one of ordinary skill in the art can easily identify such erroneous sequences by reference to the amino acid sequence of SEQ ID) NO: 2.

Within another aspect of the present invention there is provided a pharmaceutical composition comprising purified zsig39 polypeptide in combination with a pharmaceutically acceptable vehicle. This pharmaceutical composition will be used to modulate energy balance in mammals or to protect endothelial cells from injury.

The expression pattern of zsig39 polypeptide indicates expression in endothelial cell tissues. With regard to endothelial cell protection, zsig39 polypeptide may be used in organ preservation, for cryopreservation, for surgical pretreatment to prevent injury due to ischemia and/or inflammation or in like procedures. The high expression level in the small intestine suggests that zsig39 polypeptide may be an endogenous factor that protects gastrointestinal tissue from ischemic reperfusion injury. Rat, rabbit and pig models of ischemic reperfusion injury are known in the art and may be used to evaluate zsig39, agonists or antagonists thereof, antibodies, fusion proteins and fragments. For example, Golino et al., *Nature Medicine*, 2(1): 35–40, 1996, describe a myocardial model of ischemic reperfusion injury employing New Zealand white rabbits. New Zealand white rabbits have also been employed in (1) an ischemic reperfusion model of the central vein in the ear and (2) a atherosclerotic femoral artery injury model in which blood flow is reinstated by balloon angioplasty. See, for example, , Winn et al., *J. Clin. Invest.*, 92: 2042–7, 1993, and Jang et al., *Circulation*, 92(10): 3041–50, 1995.

A rat model of gut ischemia may also be employed. For example, male Sprague Dawley rats weighing between 225 and 400 grams undergo three training sessions with regard to sitting quietly in restraining cages. Next, the rats undergo a survival surgery, during which jugular vein catheters are implanted. For the survival surgery, rats are anesthetized, and catheter is implanted in the right jugular vein under conditions selected to maintain patency. The rats are then placed in restrainer cages and receive administrations of the test composition or vehicle as described below. The rats were allowed to recover for 48 hours prior to a 4 day single intravenous bolus injection (0.5 ml) per day of either vehicle or test composition. The rats are fasted, preferably for 16–24 hours, anesthetized, and given an analgesic, prior to the fourth injection. Thirty minutes after the fourth injection, the abdomen of each rat is opened with a small incision, and the superior mesenteric artery is isolated and clamped for one hour. The abdomen is lcosely sutured closed during the clamping period, reopened for removal of the clamp and again loosely sutured closed. The rats are placed into holding cages resting on a 37° C. heating pad for a two hour reperfusion period. Following the reperfusion period, the rats are sacrificed and jejunal intestinal segments are excised. Some excised intestinal segments are subject to histological evaluation and others are analyzed for myeloperoxidase (MPO) and maltase activities.

MPO is a measure of the amount of neutrophil infiltration into the tissue, while maltase activity is a measure of the integrity of the intestinal mucosa. Ischemic reperfusion injury is associated with increased levels of MPO and reduced levels of maltase activity. Consequently, amelioration of ischemic reperfusion injury is expected to result in reduced MPO and increased maltase activity.

Also, zsig39 polypeptide is expressed in the subthalamic nucleus, suggesting that zsig39 polypeptide or agonist thereof may be an endogenous suppressor of ballistic movement by delivering an inhibitory stimulus to chronically active cells. Such ballistic movements result from lesion of subthalamic nuclei. Evaluation of zsig39 polypeptide, agonists or antagonists thereof, antibodies, fusion proteins and fragments for efficacy in suppressing ballistic movements may be conducted using techniques that are known in the art. For example, stereotactic instruments can be used to lesion the subthalamic nuclei; if ballistic movement is observed, zsig39 polypeptide, agonists or antagonists thereof, antibodies, fusion proteins or fragments are administered; and any modulation of ballistic movement is noted.

With regard to modulating energy balance, zsig39 polypeptides modulate cellular metabolic reactions. Such metabolic reactions include adipogenesis, gluconeogenesis, glycogenolysis, lipogenesis, glucose uptake, protein synthesis, thermogenesis, oxygen utilization and the like. Among other methods known in the art or described herein, mammalian energy balance may be evaluated Dy monitoring one or more of the aforementioned metabolic functions. These metabolic functions are monitored by techniques (assays or animal models) known to one of ordinary skill in the art, as is more fully set forth below. For example, the glucoregulatory effects of insulin are predominantly exerted in the liver, skeletal muscle and adipose tissue. Insulin binds to its cellular receptor in these three tissues and initiates tissue-specific actions that result in, for example, the inhibition of glucose production and the stimulation of glucose utilization. In the liver, insulin stimulates glucose uptake and inhibits gluconeogenesis and glycogenolysis. In skeletal muscle and adipose tissue, insulin acts to stimulate the uptake, storage and utilization of glucose.

Art-recognized methods exist for monitoring all of the metabolic functions recited above. Thus, one of ordinary skill in the art is able to evaluate zsig39 polypeptides, fragments, fusion proteins, antibodies, agonists and antagonists for metabolic modulating functions. Exemplary modulating techniques are set forth below.

Adipogenesis, gluconeogenesis and glycogenolysis are interrelated components of mammalian energy balance, which may be evaluated by known techniques using, for example, ob/ob mice or db/db mice. The ob/ob mice are inbred mice that are homozygous for an inactivating mutation at the ob (obese) locus. Such ol/ob mice are hyperphagic and hypometabolic, and are believed to be deficient in production of circulating OB protein. The db/db mice are inbred mice that are homozygous for an inactivating mutation at the db (diabetes) locus. The db/db mice display a phenotype similar to that of ob/ob mice, except db/db mice also display a diabetic phenotype. Such db/db mice are believed to be resistant to the effects of circulating OB protein. Also, various in vitro methods of assessing these parameters are known in the art.

Insulin-stimulated lipogenesis, for example, may be monitored by measuring the incorporation of $^{14}$C-acetate into triglyceride (Mackall et al. *J. Biol. Chem.* 251:6462–6464, 1976) or triglyceride accumulation (Kletzien et al., *Mol. Pharmacol.* 41:393–398, 1992).

Glucose uptake may be evaluated, for example, in an assay for insulin-stimulated glucose transport. Non-transfected, differentiated L6 myotubes (maintained in the absence of G418) are placed in DMEM containing 1 g/l glucose, 0.5 or 1.0% BSA, 20 mM Hepes, and 2 mM glutamine. After two to five hours of culture, the medium is replaced with fresh, glucose-free DMEM containing 0.5 or 1.0% BSA, 20 mM Hepes, 1 mM pyruvate, and 2 mM glutamine. Appropriate concentrations of insulin or IGF-1, or a dilution series of the test substance, are added, and the cells are incubated for 20–30 minutes. $^3$H or $^{14}$C-labeled deoxyglucose is added to ≈50 1 M final concentration, and the cells are incubated for approximately 10–30 minutes. The cells are then quickly rinsed with cold buffer (e.g. PBS), then lysed with a suitable lysing agent: (e.g. 1% SDS or 1 N NaOH). The cell lysate is then evaluated by counting in a scintillation counter. Cell-associated radioactivity is taken as a measure of glucose transport after subtracting non-specific binding as determined by incubating cells in the presence of cytocliolasin b, an inhibitor of glucose transport. Other methods include those described by, for example, Manchester et al., *Am. J. Physiol.* 266 (Endocrinol. Metab. 29):E326-E333, 1994 (insulin-stimulated glucose transport).

Fatty acid metabolism may also be monitored by techniques known in the art. In particular, uptake and metabolism of fatty acids by the heart. Suitable animal models are available and tissues are available. Cultured cells include cardiac fibroblasts and cardiac myocytes. Established cell lines include: NIH 3T3 fibroblast (ATCC No. CRL-1658), CHH-1 chum heart cells (ATCC No. CRL-1680) and H9c2 rat heart myoblasts (ATCC No. CRL-1446). It has been demonstrated that as cardiac cells age there is a shift from fatty acid metabolism to glucose metabolism (Sack et al., *Circulation* 94:2837–42, 1996).

Protein synthesis may be evaluated, for example, by comparing precipitation of $^{35}$S-methionine-labeled proteins following incubation of the test cells with $^{35}$S-methionine and $^{35}$S-methionine and a putative modulator of protein synthesis.

Thermogenesis may be evaluated as described by B. Stanley in *The Biology of Neuropeptide Y and Related Peptides*, W. Colmers and C. Wahlestedt (eds.), Humana Press, Ottawa, 1993, pp. 457–509; C. Billington et al., *Am. J. Physiol.* 260:R321, 1991; N. Zarjevski et al., *Endocrinology* 133:1753, 1993; C. Billington et al., *Am. J. Physiol.* 266:R1765, 1994; Heller et al., *Am. J. Physiol.* 252(4 Pt 2): R661–7, 1987; and Heller et al., *Am. J. Physiol.* 245(3): R321–8, 1983. Also, metabolic rate, which may be measured by a variety of techniques, is an indirect measurement of thermogenesis.

Oxygen utilization may be evaluated as described by Heller et al., *Pflugers Arch* 369(1): 55–9, 1977. This method also involved an analysis of hypothalmic temperature and metabolic heat production. Oxygen utilization and thermoregulation have also been evaluated in humans as described by Haskell et al., *J. Appl. Physiol.* 51(4): 948–54, 1981.

Expression of zsig39 polypeptide in the heart and in brain tissue involved in involuntary function (i.e., the medulla oblongata) suggests that the protein may modulate acetylcholine and/or norepinephrine release. Among other methods known in the art or described herein, mammalian endothelial cell tissue protection may be evaluated by monitoring the function of endothelial tissue. For example, the function of the heart (aorta) may be evaluated by monitoring acetylcholine release, norepinephrine release or like parameters. These parameters are monitored by techniques (assays or animal models) known to one of ordinary skill in the art, as is more fully set forth below.

Acetylcholine and norepinephrine release may be monitored by HPLC. Levy, *Electrophysiclogy of the Sinoatrial and Atrioventricular Nodes*, Alan R. Liss, Inc., 187–197, 1998, describe measurement of norepinephrine in coronary sinus effluent. In addition, animals may be electrically paced, with the results monitored as described by Elsner, *European Heart Journal* 16(Supplement N) 52–8, 1995, and Reiffel and Kuehnert, *PACE* 17 (Part 1): 349–65, 1994.

Zsig39 polypeptides may also find use as neurotransmitters or as modulators of neurctransmission, as indicated by expression of the polypepticle in tissues associated with the sympathetic or parasympathetic nervous system. In this regard, zsig39 polypeptides may find utility in modulating nutrient uptake, as demonstrated, for example, by 2-deoxy-glucose uptake in the brain or the like.

Among other methods known in the art or described herein, neurotransmission functions may be evaluated by monitoring 2-deoxy-glucose uptake in the brain. This parameter is monitored by techniques (assays or animal models) known to one of ordinary skill in the art, for example, autoradiography. Useful monitoring techniques are described, for example, by Kilduff et al., *J. Neurosci.* 10 2463–75, 1990, with related techniques used to evaluate the "hibernating heart" as described in Gerber et al. *Circulation* 94(4): 651–8, 1996, and Fallavollita et al., *Circulation* 95(7): 1900–1909, 1997.

In addition, zsig39 polypeptides, fragments, fusions agonists or antagonists thereof may be therapeutically useful for anti-microbial or neurotransmitter-modulated applications. For example, complement component C1q plays a role in host defense against infectious agents, such as bacteria and viruses. C1q is known to exhibit several specialized functions. For example, C1q triggers the complement cascade via interaction with bound antibody or C-reactive protein (CRP). Also, C1q interacts directly with certain bacteria, RNA viruses, mycoplasma, uric acid crystals, the lipid A component of bacterial endotoxin and membranes of certain intracellular organelles. C1q binding to the C1q receptor is believed to promote phagocytosis. C1q also appears to enhance the antibody formation aspect of the host defense system. See, for example, Johnston, *Pediatr. Infect. Dis. J.* 12(11): 933–41, 1993. Thus, soluble C1q-like molecules may be useful as anti-microbial agents, promoting lysis or phagocytosis of infectious agents.

The zsig39 polypeptides of the present invention also exhibit homology to moieties believed to modulate neurotransmission. As shown in FIG. 1, zsig39 polypeptides are homologous to the following proteins: HP25_TAMAS (SEQ ID NO:5) (Takamatsu et al., *Mol. Cell. Biol.* 13: 1516–21, 1993 and Kondo & Kondo, *J. Biol. Chem.* 267: 473–8, 1992); HP27_TAMAS (SEQ ID NO:6) (Takamatsu et al. and Kondo & Kondo referenced above) and CERL_RAT (SEQ ID NO:7) (Wada & Ohtani, *Brain Res. Mol. Brain Res.* 9: 71–7, 1991). HP25 and HP27 are polypeptides found in the active (summer) serum of hibernating Siberian woodchucks. CERL is present in the rat cerebellum. Thus, zsig39 polypeptides, fragments, fusions, agonists or antagonists may be useful in modulating neurotransmission by, for example, binding to neurotransmitters or receptors therefor.

Radiation hybrid mapping is a somatic cell genetic technique developed for constructing high-resolution, contiguous maps of mammalian chromosomes (Cox et al., *Science* 250:245–250, 1990). Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other nonpolymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

The results showed that the zsig39 polypeptide-encoding gene maps 549.99 cR_3000 from the top of the human chromosome 11 linkage group on the WICGR radiation hybrid map. Proximal and distal framework markers were AFMB048ZA9 and FB17D4, respectively. The use of surrounding markers positions the zsig39 gene in the 11q23.3 region on the integrated LDB chromosome 11 map (The Genetic Location Database, University of Southhampton, WWW server:http://cedar.genetics.soton.ac.uk/public_html/).

The present invention also provides reagents which will find use in diagnostic applications. For example, the zsig39 gene, a probe comprising zsig39 DNA or RNA or a subsequence thereof can be used to determine if the zsig39 gene is present on chromosome 11 or if a mutation has occurred. Detectable chromosomal aberrations at the zsig39 gene locus include but are not limited to aneuploidy, gene copy number changes, insertions, deletions, restriction site changes and rearrangements.

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., *ibid.*; Ausubel et. al., *ibid.*; Marian, *Chest* 108:255–65, 1995). Ribonuclease protection assays (see, e.g., Ausubel et al., *ibid.*, ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–8, 1991).

Zsig39 polypeptides may be used in the analysis of energy efficiency of a mammal. Zsig39 polypeptides found in serum or tissue samples may be indicative of a mammals ability to store food, with more highly efficient mammals tending toward obesity. More specifically, the present invention contemplates methods for detecting zsig39 polypeptide comprising:

exposing a sample possibly containing zsig39 polypeptide to an antibody attached to a solid support, wherein said antibody binds to an epitope of a zsig39 polypeptide;

washing said immobilized antibody-polypeptide to remove unbound contaminants;

exposing the immobilized antibody-polypeptide to a second antibody directed to a second epitope of a zsig39 polypeptide, wherein the second antibody is associated with a detectable label; and detecting the detectable label. The concentration of zsig39 polypeptide in the test sample appears to be indicative of the energy efficiency of a mammal. This information can aid nutritional analysis of a mammal. Potentially, this information may be useful in identifying and/or targeting energy deficient tissue.

As is described in greater detail below, mice receiving zsig39 were found to have decreased levels of serum free fatty acids and a increase in bone fat. Fatty acids are incorporated into triglycerides and stored as fat. The stored fat acts to insulate the body from heat loss and protect internal organs. Fat also serves as a repository of stored energy. Fatty acids are released from the triglycerides by hormone-regulated lipases for use in energy metabolism. Decrease in free fatty acid levels suggests zsig39 has an effect on the uptake and metabolism of free fatty acids. Zsig39 may act to inhibit the of release of fatty acids from fat reserves, such as by inhibiting the action of hormonal lipases. Zsig39 may also act to enhance fatty acid uptake, metabolism and storage. Zsig39 may act independently or in concert with other molecules, such as insulin, to inhibit lipolysis, enhance fatty acid uptake and/or metabolism. As such, zsig39 would be useful in regulation of energy metabolism. The invention therefore provides a method for modulating free fatty acid metabolism in individuals in need of such treatment by administering to such an individual a pharmaceutically effective dose of a zsig39 polypeptide. A "pharmaceutically effective amount" of a zsig39 polypeptide is an amount sufficient to induce a desired biological result. The result can be alleviation of the signs, symptoms, or causes of a disease, or any other desired alteration of a biological system. For example, an effective amount of a zsig39 polypeptide, agonist or antagonist is that which provides either subjective relief of symptoms or an objectively identifiable improvement as noted by the clinician or other qualified observer. In particular, such an effective amount of a zsig39 polypeptide results in reduction serum free fatty acid levels or other beneficial effect. Effective amounts of the zsig39 polypeptides can vary widely depending on the disease or symptom to be treated. The amount of the polypeptide to be administered, and its concentration in the formulations, depends upon the vehicle selected, route of administration, the potency of the particular polypeptide, the clinical condition of the patient, the side effects and the stability of the compound in the formulation. Thus, the clinician will employ the appropriate preparation containing the appropriate concentration in the formulation, as well as the amount of formulation administered, depending upon clinical experience with the patient in question or with similar patients. Such amounts will depend, in part, on the particular condition to be treated, age, weight, and general health of the patient, and other factors evident to those skilled in the art.

Within additional aspects of the invention there are provided antibodies or synthesized binding proteins(e.g., those generated by phage display, E.coli Fab, and the like) that specifically bind to the zsig39 polypeptides described above. Such antibodies are useful for, among other uses as described herein, preparation of anti-idiotypic antibodies. Synthesized binding proteins may be produced by phage display using commercially available kits, such as the Ph.D.™ Phage Display Peptide Library Kits available from New England Biolabs, Inc. (Beverly, Mass.). Phage display techniques are described, for example, in U.S. Pat. Nos. 5,223,409, 5,403,484 and 5,571,698.

An additional aspect of the present invention provides methods for identifying agonists or antagonists of the zsig39 polypeptides disclosed above, which agonists or antagonists may have valuable properties as discussed further herein.

Within one embodiment, there is provided a method of identifying zsig39 polypeptide agonists, comprising providing cells responsive thereto, culturing the cells in the presence of a test compound and comparing the cellular response with the cell cultured in the presence of the zsig39 polypeptide, and selecting the test compounds for which the cellular response is of the same type.

Within another embodiment, there is provided a method of identifying antagonists of zsig39 polypeptide, comprising providing cells responsive to a zsig39 polypeptide, culturing a first portion of the cells in the presence of zsig39 polypeptide, culturing a second portion of the cells in the presence of the zsig39 polypeptide and a test compound, and detecting a decrease in a cellular response of the second portion of the cells as compared to the first portion of the cells.

In addition to those assays disclosed herein, samples can be tested for inhibition of zsig39 activity within a variety of assays designed to measure receptor binding or the stimulation/inhibition of zsig39-dependent cellular responses. For example, zsig39-responsive cell lines can be transfected with a reporter gene construct that is responsive to a zsig39-stimulated cellular pathway. Reporter gene constructs of this type are known in the art, and will generally comprise a zsig39-DNA response element operably linked to a gene encoding an assayable protein, such as luciferase. DNA response elements can include, but are not limited to, cyclic AMP response elements (CRE), hormone response elements (HRE) insulin response element (IRE) (Nasrin et al., Proc. Natl. Acad. Sci. USA 87:5273–7, 1990) and serum response elements (SRE) (Shaw et al. Cell 56: 563–72, 1989). Cyclic AMP response elements are reviewed in Roestler et al., J. Biol. Chem. 263 (19):9063–6; 1988 and Habener, Molec. Endocrinol. 4 (8):1087–94; 1990. Hormone response elements are reviewed in Beato, Cell 56:335–44; 1989. Candidate compounds, solutions, mixtures or extracts are tested for the ability to inhibit the activity of zsig39 on the target cells as evidenced by a decrease in zsig39 stimulation of reporter gene expression. Assays of this type will detect compounds that directly block zsig39 binding to cell-surface receptors, as well as compounds that block processes in the cellular pathway subsequent to receptor-ligand binding. In the alternative, compounds or other samples can be tested for direct blocking of zsig39 binding to receptor using zsig39 tagged with a detectable label (e.g., $^{125}$I, biotin, horseradish peroxidase, FITC, and the like). Within assays of this type, the ability of a test sample to inhibit the binding of labeled zsig39 to the receptor is indicative of inhibitory activity, which can be confirmed through secondary assays. Receptors used within binding assays may be cellular receptors or isolated, immobilized receptors.

A further aspect of the invention provides a method for studying insulin. Such methods of the present invention comprise incubating adipocytes in a culture medium comprising zsig39 polypeptide, monoclonal antibody, agonist or antagonist thereof±insulin and observing changes in adipocyte protein secretion or differentiation.

Anti-microbial protective agents may be directly acting or indirectly acting. Such agents operating via membrane association or pore forming mechanisms of action directly attach to the offending microbe. Anti-microbial agents can also act via an enzymatic mechanism, breaking down microbial protective substances or the cell wall/membrane thereof. Anti-microbial agents, capable of inhibiting microorganism proliferation or action or of disrupting microorganism integrity by either mechanism set forth above, are useful in methods for preventing contamination in cell culture by microbes susceptible to that anti-microbial activity. Such techniques involve culturing cells in the presence of an effective amount of said zsig39 polypeptide or an agonist or antagonist thereof.

Also, zsig39 polypeptides or agonists thereof may be used as cell culture reagents in in vitro studies of exogenous microorganism infection, such as bacterial, viral or fungal infection. Such moieties may also be used in in vivo animal models of infection.

The present invention also provides methods of studying mammalian cellular metabolism. Such methods of the present invention comprise incubating cells to be studies, for example, human vascular endothelial cells, ± zsig39 polypeptide, monoclonal antibody, agonist or antagonist thereof and observing changes in adipogenesis, gluconeogenesis, glycogenolysis, lipogenesis, glucose uptake, or the like.

An additional aspect of the invention provides a method for studying dimerization or oligomerization. Such methods of the present invention comprise incubating zsig39 polypeptides or fragments or fusion proteins thereof containing a collagen-like domain alone or in combination with other polypeptides bearing collagen-like domains and observing the associations formed between the collagen like domains. Thus, both homomeric and heteromeric constructs may be studied in this manner. Such associations are indicated by HPLC, circular dichroism or the like.

As previously noted, the isolated polynucleotides of the present invention include DNA and RNA. Methods for isolating DNA and RNA are well known in the art. It is generally preferred to isolate RNA from brain tumor, heart, placenta, adipose tissue and the like, although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly(A)$^+$ RNA using known methods. Polynucleotides encoding zsig39 polypeptides are then identified and isolated by, for example, hybridization or PCR.

The present invention further provides counterpart polypeptides and polynucleotides from other species (orthologs). These species include, but are not limited to mammalian, avian, amphibian, reptile, fish, insect and other vertebrate and invertebrate species. Of particular interest are zsig39 polypeptides from other mammalian species, including murine, rat, porcine, ovine, bovine, canine, feline, equine and other primate proteins. Orthologs of the human proteins can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue of cell line. A zsig39 polypeptide-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to zsig39 polypeptide. Similar techniques can also be applied to the isolation of genomic clones.

Those skilled in the art will recognize that the sequences disclosed in SEQ ID NO:1 and SEQ ID NO:2 represent a single allele of human zsig39 DNA and protein and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the zsig39 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated zsig39 polypeptides that are substantially homologous to the polypeptides of SEQ ID NO:2 and their species orthologs. The term "substantially homologous" is used herein to denote polypeptides having 50%, preferably 60%, more preferably at least 80%, sequence identity to the sequences shown in SEQ ID NO:2 or their orthologs. Such polypeptides will more preferably be al least 90% identical, and most preferably 95% or more identical to SEQ ID NO:2 or its orthologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (*ibid.*) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |

TABLE 3-continued

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 9 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypEptide; small deletions, typically of one to about 30 amino acids; and small amino- or carboxyl-terminal extensions, such as an amino-terminal methionine residue, a small linker peptide of up to about 20–25 residues, or a small extension that facilitates purification, an affinity tag. Polypeptides comprising affinity tags can further comprise a proteolytic cleavage site between the zsig39 polypeptide and the affinity tag. Preferred such sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise non-naturally occurring amino acid residues. Non-naturally occurring amino acids include, without limitation, trans-3-methylproline, 2,4-methanoproline, cis-4-hydroxy-proline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for zsig39 amino acid residues.

Essential amino acids in the polypeptides of the present invention can be identified according to procedures known in the art, such as site-directed mutagenesis or alanine-scanning mutagenesis (Cunningham and Wells, *Science* 244: 1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity (e.g., ability to modulate energy balance) as disclosed below to identify amino acid residues that are critical to the activity of the molecule. See also, Hilton et al., *J. Biol. Chem.* 271:4699–708, 1996. Sites of ligand-receptor or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of horologies with related polypeptides.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zsig39 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput, automated screening methods to detect activity of cloned, mutagenized polypeptides in host cells. Mutagenized DNA molecules that encode active polypeptides (e.g., ability to modulate energy balance) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are substantially homologous to residues 19 to 243 of SEQ ID NO:2 or allelic variants thereof and retain the energy balance modulating or other properties of the wild-type protein. Such polypeptides may include additional amino acids, such as additional collagen repeats of the Gly-Xaa-Pro or Gly-Xaa-Xaa type. Such polypeptides may also include additional polypeptide segments as generally disclosed above.

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al. (eds.), *Current Protocols in Molecular Biology*, John Wiley and Sons, Inc., N.Y., 1987.

In general, a DNA sequence encoding a zsig39 polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zsig39 polypeptide into the secretory pathway of a host cell, a secretory signal sequence (also known as a leader sequence, prepro sequence or pre sequence) is provided in the expression vector. The secretory signal sequence may be that of the zsig39 polypeptide, or may be derived from another secreted protein (e.g., t-PA) or synthesized de novo. The secretory signal sequence is joined to the zsig39 polypeptide DNA sequence in the correct reading frame and positioned to direct the newly synthesized polypeptide into he secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid residues 1–15 or 1–19 of SEQ ID NO:2 is be operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally nonsecreted protein, such as a receptor. Such fusions may be used in vivo or in vitro to direct peptides through the secretory pathway.

Cultured mammalian cells are also suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J*. 1:841–845, 1982), DEAE-dextran mediated transfection (Ausubel et al., eds., *Current Protocols in Molecular Biology*, John Wiley and Sons, Inc., N.Y., 1987), liposome-mediated transfection (Hawley-Nelson et al., *Focus* 15:73, 1993; Ciccarone et al., *Focus* 15:80, 1993), and viral vectors (Miller and Rosman, *BioTechniques* 7:980–90, 1989; Wang and Finer, *Nature Med*. 2:714–16, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Preferred cultured mammalian cells include the COS-1 (ATCC No. CRL 1650), COS-7 (ATCC No. CRL 1651), BHK 570 ATCC No. CRL 10314), 293 (ATCC No. CRL 1573; Graham et al., *J. Gen. Virol*. 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothioneiri genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing thLe amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci*. (Bangalore) 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica nuclear polyhedrosis* virus (AcNPV). See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant zsig39 baculovirus utilizes a transposon-based system described by Luckow (Luckow et al., *J. Virol*. 67:4566–79, 1993). This system, which utilizes transfer vectors, is sold in the Bac-to-Bac™ kit (Life Technologies, Rockville Md.). This system utilizes a transfer vector, pFast-Bac1™ (Life Technologies) containing a Tn7 transposon to move the DNA encoding the zsig39 polypeptide into a baculovirus genome maintained in *E. coli* as a large plasmid called a "bacmid." See, Hill-Perkins and Possee, *J. Gen. Virol*. 71:971–6, 1990; Bonning et al., *J. Gen. Virol*. 75:1551–6, 1994; and, Chazenbalk and Rapoport, *J. Biol. Chem*. 270:1543–9, 1995. In addition, transfer vectors can include an in-frame fusion with DNA encoding an epitope tag at the C- or N-terminus of the expressed zsig39 polypeptide, for example, a Glu-Glu epitope tag (Grussenmeyer et al., *Proc. Natl. Acad. Sci*. 82:7952–4, 1985). Using a technique known in the art, a transfer vector containing zsig39 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zsig39 is subsequently produced. Recombinant viral stocks are made by methods commonly used the art.

The recombinant virus is used tc infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. #5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3. Procedures used are generally described in available laboratory manuals (King and Possee, *ibid*.; O'Reilly et al., *ibid*.; Richardson, *ibid*.). Subsequent purification of the zsig39 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in Saccharomyces cerevisiae is the POT1 vector system disclosed by Kawasaki et al. (U.S. Pat. No. 4,931,373), which allows transformed cells to be selected by growth in glucose-containing media. Suitable promoters and terminators for us.e in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S.

Pat. Nos. 4,990,446; 5,063,154; 5.139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\pi$) of from 1 to 40 milliseconds, most preferably about 20 milliseconds.

Prokaryotic host cells, includinc strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., *ibid.*). When expressing a zsig39 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Expressed recombinant zsig39 polypeptides (or chimeric zsig39 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Suitable chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimicle coupling chemistries. These and other solid media are well known and widely used in the art, and are available from commercial suppliers. Methods for bind ng receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their structural or binding properties. For example, immobilized metal ion adsorption (IMAC) chromatography can be used to purify histidine-rich proteins, or proteins having His tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Eiego, 1990, pp.529–39). Within additional embodiments of the invention, a fusion of the polypeptide of interest and an affinity tag (e.g., Glu-Glu affinity tags, FLAG tags, maltose-binding protein, an immunoglobulin domain) may be constructed to facilitate purification. Such purification methods are disclosed in detain in the Example section below.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Zsig39 polypeptides or fragments thereof may also be prepared through chemical synthesis. Such zsig39 polypeptides may be monomers or multimers; glycosylated or non-glycosylated; pegylated or non-pegylated; and may or may not include an initial methionine amino acid residue.

An in vivo approach for assaying proteins of the present invention involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161–89, 1994; and Douglas and Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologou DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenoviras primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained.

A ligand-binding polypeptide, such as a zsig39 polypeptide-binding polypeptide, can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the ligand-binding polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore™, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

As would be evident to one of ordinary skill in the art, polyclonal antibodies can be generated from inoculating a variety of warm-blooded animals such as horses, cows, goats, sheep, dogs, chickens, rabbits, mice, hamsters, guinea pigs and rats as well as transgenic animals such as transgenic sheep, cows, goats or pigs. Antibodies may also be expressed in yeast and fungi in modified forms as well as in mammalian and insect cells. The zsig39 polypeptide or a fragment thereof serves as an antigen (immunogen) to inoculate an animal or elicit an immune response. Suitable antigens would include the zsig39 polypeptide encoded by SEQ ID NO:2 from amino acid residue 16–2243 of SEQ ID NO:2, from amino acid residue 19–243 of SEQ ID NO:2, or a contiguous 9–243 amino acid residue fragment thereof. The immunogenicity of a zsig39 polypeptide may be increased through the use of an adjuvant, such as alum (aluminum hydroxide) or Freund's complete or incomplete adjuvant. Polypeptides useful for immunization also include fusion polypeptides, such as fusions of zsig39 or a portion thereof with an immunoglobulin polypeptide or with an affinity tag. The polypeptide immunogen mass be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and anligen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and cons-ant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to zsig39 protein or peptide, and selection of antibody display libraries in phage or similar vectors (for instance, through use of immobilized or labeled zsig39 protein or peptide).

Antibodies are defined to be specifically binding if: 1) they exhibit a threshold level of binding activity, and/or 2) they do not significantly cross-react with related polypeptide molecules. First, antibodies herein specifically bind if they bind to a zsig39 polypeptide, peptide or epitope with a binding affinity ($K_a$) of $10^6$ mol-1 or greater, preferably $10^7$ mol$^{-1}$ or greater, more preferably $10^8$ mol$^{-1}$ or greater, and most preferably $10^9$ mol$^{-1}$ or greater. The binding affinity of an antibody can be readily determined by one of ordinary skill in the art, for example, by Scatchard analysis (Scatchard, *Ann. NY Acad. Sci.* 51: 660–72, 1949).

Second, antibodies specifically bind if they do not significantly cross-react with related polypeptides. Antibodies do not significantly cross-react with related polypeptide molecules, for example, if they detect zsig39 polypeptide but not known related polypept:Ldes using a standard Western blot analysis (Ausubel et al., *ibid.*). Examples of known related polypeptides are orthologs, proteins from the same species that are members of a protein family such as Acrp30 (SEQ ID NO:8), the polypeptides shown in alignment FIG. 1, mutant human zsig39 polypeptides, and the like. Moreover, antibodies may be "screened against" known related polypeptides to isolate a population that specifically binds to the inventive polypeptides. For example, antibodies raised to human zsig39 polypeptides are adsorbec to related polypeptides adhered to insoluble matrix; antibodies specific to human zsig39 polypeptides will flow through the matrix under the proper buffer conditions. Such screening allows isolation of polyclonal and monoclonal antibodies noncrossreactive to closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art (see, Fundamental Immunology, Paul (eds.), Raven Press, 1993; Getzoff et al., *Adv. in Immunol.* 43: 1–98, 1988; *Monoclonal Antibodies: Principles and Practice*, Goding, J. W. (eds.), Academic Press Ltd., 1996; Benjamin et al., *Ann. Rev. Immunol.* 2: 67–101, 1984). Representative examples of such assays include: concurrent immunoelectrophoresis, radioimmuno-assay, radioimmuno-precipitation, enzyme-linked immuno-sorbent assay (ELISA), dot blot or Western blot assay, inhibition or competition assay, and sandwich assay.

Genes encoding polypeptides having potential zsig39 polypeptide binding domains, "bindirg proteins", can be obtained by screening random or directed peptide libraries displayed on phage (phage display) or on bacteria, such as *E. coli*. Nucleotide sequences encoding the polypeptides can be obtained in a number of ways, such as through random mutagenesis and random polynucleotide synthesis. Alternatively, constrained phage display libraries can also be produced. These peptide display libraries can be used to screen for peptides which interact with a known target which can be a protein or polypeptide, such as a ligand or receptor, a biological or synthetic macromolecule, or organic or inorganic substances. Techniques for creating and screening such peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscalaway, N.J.). Peptide display libraries can be screened using the zsig39 sequences disclosed herein to identify proteins which bind to zsig39. These "binding proteins" which interact with zsig39 polypeptides can be used essentially like an antibody, for tagging cells; for isolating homolog polypeptides by affinity purification; directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. To increase the half-life of these binding proteins, they can be conjugated. Their biological properties may be modified by dimerizing or multimerizing for use as agonists or antagonists. Binding peptides can be screened against known related polypeptides as described above.

Antibodies and binding proteins to zsig39 may be used for tagging cells that express zsig39; for isolating zsig39 by affinity purification; for diagnostic assays for determining circulating levels of zsig39 polypeptides; for detecting or quantitating soluble zsig39 as marker of underlying pathology or disease; in analytical methods employing FACS; for screening expression libraries; for generating anti-idiotypic antibodies; and as neutralizing antibodies or as antagonists to block zsig39 polypeptide energy balance modulation activity or like activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Moreover, antibodies to zsig39 or fragments thereof may be used in vitro to detect denatured zsig39 or fragments thereof in assays, for example, Western Blots or other assays known in the art.

Antibodies or binding proteins herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zsig39 polypeptides or anti-zsig39 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adramycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anticomplementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates. The bioactive polypeptide or antibody conjugates described herein can be delivered intravenously, intraarterially, intraductally with DMSO, intramuscularly, subcutaneously, intraperitcneally, also by transdermal methods, by electro-transfer, orally or via inhalant.

Polynucleotides encoding zsig39 polypeptides are useful within gene therapy applications where it is desired to increase or inhibit zsig39 activity. If a mammal has a mutated or absent zsig39 gene, the zsig39 gene can be introduced into the cells of the mammal. In one embodiment, a gene encoding a zsig39 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zsig39 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; WIPO Publication WO 95/07358; and Kuo et al., *Blood* 82:845, 1993. Alterratively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zsig39 gene transcription, such as to inhibit cell proliferation in viva. Polynucleotides that are complementary to a segment of a zsig39-encoding polynucleotide (e.g., a polynucleotide as set froth in SEQ ID NO:1) are designed to bind to zsig39-encoding mRNA and to inhibit translation of such mRNA. Such antisense polynucleotides are used to inhibit expression of zsig39 polypeptide-encoding genes in cell culture or in a subject.

Transgenic mice, engineered to express the zsig39 gene, and mice that exhibit a complete absence of zsig39 gene function, referred to as "knockout mice" (Snouwaert et al., *Science* 257:1083, 1992), may also be generated (Lowell et al., *Nature* 366:740–42, 1993). These mice may be employed to study the zsig39 gene and the protein encoded thereby in an in vivo system.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a zsig39 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton Pa., 19$^{th}$ ed., 1995. Therapeutic doses will generally be determined by the clinician according to accepted standards, taking into account the nature and severity of the condition to be treated, patient traits, etc. Determination of dose is within the level of ordinary skill in the art.

The invention is further illustrated by the following non-limiting examples.

EXAMPLE 1

Extension of EST Sequence

The novel zsig39 polypeptide-encoding polynucleotides of the present invention were initially identified by selecting an EST from an EST database, predicting a protein sequence based thereupon, and searching known sequence databases for the secreted protein that is most homologous to predicted protein based on the EST. ESTs that potentially encode proteins having biologically interesting homology to known secreted proteins were identified for further study. A single EST sequence was discovered and predicted to be homologous to adipocyte specific protein. See, for example, Scherer et al., *J. Biol. Chem.* 270(45): 26746–9, 1995. To identify the corresponding cDNA, a clone considered likely to contain the entire coding sequence was used for sequencing. Using an Invitrogen S.N.A.P.™ Miniprep kit (Invitrogen, Corp., San Diego, Calif.) according to manufacturer's instructions a 5 ml overnight culture in LB+50 µg/ml ampicillin was prepared. The template was sequenced on an ABIPRISM™ model 377 ENA sequencer (Perkin-Elmer Cetus, Norwalk, Conn.) using the ABI PRISM™ Dye Terminator Cycle Sequencing Ready Reaction Kit (Perkin-Elmer Corp.) according to manufacturer's instructions. Oligonucleotides ZC447 (SEQ ID NO:11), ZC976 (SEQ ID NO:12) to the M13 and lacZ promoters on the clone-containing vector were used as sequencing primers. Oligonucleotides ZC14707 (SEQ ID NO:13), ZC14708 (SEQ ID NO:14), ZC14760 (SEQ ID NO:15), ZC14758 (SEQ ID NO:16) and ZC14759 (SEQ ID NO:17) were used to complete the sequence from the clone. Sequencing reactions were carried out in a Hybaid OmniGene Temperature Cycling System (National Labnet Co., Woodbridge, N.Y.). SEQUENCHER™ 3.1 sequence analysis software (Gene Codes Corporation, Ann Arbor, Mich.) was used for data analysis. The resulting 1347 bp sequence is disclosed in SEQ ID NO: 1. Comparison of the originally derived EST sequence with the sequence represented in SEQ ID NO:1 showed that there were 27 base pair differences which resulted in 11 amino acid differences between the deduced amino acid sequences. Note that 22 of the base pair differences were from unknown "N" residues in the EST sequence to known residues in SEQ ID NO:1, which result in "assumed" amino acid changes.

EXAMPLE 2

Tissue Distribution

Northerns were performed using Human Multiple Tissue Blots from Clontech (Palo Alto, Calif.). An approximately 1347 bp DNA probe, corresponding to the a sequence encompassing a polynucleotide encoding full length zsig39 polypeptide, generated by EcoR1-NotI digest of the plasmid DNA. The resulting fragment was gel purified for use as a probe. The DNA probe was radioactively labeled with $^{32}$P using REDIPRIME® DNA labeling system (Amersham, Arlington Heights, Ill.) according to the manufacturer's specifications. The probe was purified using a NUCTRAP push column (Stratagene Cloning Systems, La Jolla, Calif.). EXPRESSHYB (Clontech, Palo Alto, Calif.) solution was used for prehybridization and as a hybridizing solution for the Northern blots. Hybridization took place overnight at 65° C., and the blots were then washed in 2×SSC and 0.1% SDS at room temperature, followed by a wash in 0.1×SSC and 0.1% SDS at 65° C. One transcript size was observed at approximately 1.2 kb. Signal intensity was highest for small intestine and heart, with relatively less intense signals in pancreas, skeletal muscle, kidney and thyroid, and with lower intensity signals in placenta, lung, liver, spleen, prostate, ovary, colon, stomach, spinal cord, lymph node, trachea, adrenal gland and bone marrow.

Additional Northern Blot Analysis was done using a Gut Northern Tissue Blot. The blot was prepared using mRNA from human colorectal adenocarcinoma cell line SW480 (Clontech, Palo Alto, Calif.), human small intestine tissue (Clontech), human stomach tissue (Clontech), human intestinal smooth muscle cell line (Hism; ATCC No.CRL-1692; American Type Culture Collection, 12301 Parklawn Drive, Rockville, Md.), normal human colon cell line (FHC; ATCC No. CRL-1831; American Type Culture Collection) and human normal fetal small intestine cell line (FHs74 Int.; ATCC No. CCL241; American Type Culture Collection).

Total RNAs were isolated from Hism, FHC and FHs74 Int. by acid guanidium method (Cheomczynski et al., *Anal. Biochem.* 162:156–9, 1987). The polyA$^+$ RNAs were selected by eluting total RNA through a column that retains polyA$^+$ RNAs (Aviv et al., *Proc. Nat. Acad. Sci.* 69:1408–12, 1972). 2 µg of polyA$^+$ RNA from each sample was separated out in a 1.5% agarose geL in 2.2 M formaldehyde and phosphate buffer. The RNAs were transferred onto Nytran membrane (Schleicher and Schuell, Keene, N.H.) in 20×SSC overnight. The blot was treated in the UV Stratalinker 2400 (Stratagene, La Jolla, Calif.) at 0.12 Joules. The bolt was then baked at 80° C. for one hour.

The Northern blots were probed with the zsig39 PCR fragment (described below in Example 4) encoding the mature zsig39 polypeptide, which was radiolabeled with $^{32}$P dCTP using a Rediprime pellet kit (Amersham, Arlington Heights, Ill.) according to the manufacturer's specifications. The blot was hybridized in EXPRESSHYB (Clontech) at 56° C. overnight. The blot was washed at room temperature in 2×SSC and 0.1 SDS, then in 2×SSC and 0.1% SDS at 65° C., and finally at 65° C. in 0.1×SSC and 0.1% SDS. Results showed that zsig39 hybridized to all tissues except the human intestinal smooth muscle cell line HISM.

EXAMPLE 3

Chromosomal Mapping of the Zsig39 Gene

The zsig39 polypeptide-encoding gene was mapped to chromosome 11 using the commercially available "GeneBridge 4 Radiation Hybrid Panel" (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of the zsig39 gene with the "GeneBridge 4 RH Panel", 20 μl reactions were set up in a PCRable 96-well microtiter plate (Stratagene, La Jolla, Calif.) and used in a "RoboCycler Gradient 96" thermal cycler (Stratagene). Each of the 95 PCR reactions consisted of 2 μl 10×KlenTaq PCR reaction buffer (CLONTECH Laboratories, Inc., Palo Alto, Calif.), 1.6 μl dNTPs mix (2.5 mM each, PERKIN-ELMER, Foster City, Calif.), 1 μl sense primer, ZC15002 (SEQ ID NO:18), 1 μl antisense primer, ZC15003 (SEQ ID NO:19), 2 μl RediLoad (Research Genetics, Inc., Huntsville, Ala.), 0.4 μl 50×Advantage Klen-Taq Polymerase Mix (Clontech Laboratories, Inc.), 25 ng of DNA from an individual hybrid clone or control and ddH$_2$O for a total volume of 20 μl. The reactions were overlaid with an equal amount of mineral oil and sealed. The PCR cycler conditions were as follows: an initial 1 cycle 5 minute denaturation at 95° C., 40 cycles of a 1 minute denaturation at 95° C., 1 minute annealing at 64° C. and 1.5 minute extension at 72° C., followed by a final 1 cycle extension of 7 minutes at 72° C. The reactions were separated by electrophoresis on a 2% agarose gel (Life Technologies, Gaithersburg, Md.).

The results showed that the zsig39 polypeptide-encoding gene maps 549.99 cR_3000 from the top of the human chromosome 11 linkage group on the WICGR radiation hybrid map. Proximal and distal framework markers were AFMB048ZA9 and FB17D4, respectively. The use of surrounding markers positions the zsig39 gene in the 11q23.3 region on the integrated LDB chromosome 11 map (The Genetic Location Database, University of Southhampton, www server: http://ceciar.genetics. soton.ac.uk/public_html/).

EXAMPLE 4

Construction of zsig39 Mammalian Expression Vectors zsig39CEE/pZP9 and zsig39NEE/pZP9

Two expression vectors were prepared for the zsig39 polypeptide, zsig39CEE/pZP9 and zsig39NEE/pZP9, wherein the constructs are designed to express a zsig39 polypeptide with a C- or N-terminal Glu-Glu tag (SEQ ID NO:20).

Zsig39NEE/pZP9

A 690 bp PCR generated zsig39 DNA fragment was created using ZC15037 (SEQ ID NO:21) and ZC15038 (SEQ ID NO:22) as PCR primers and colonies described above as a template. An N-terminal Glu-Glu tag and restriction sites Bam HI and Xba I are added. PCR amplification of the zsig39 fragment were 94° C. for 90 seconds, 5 cycles of 94° C. for 10 seconds, 34° C. for 20 seconds, 74° C. for 40 seconds followed by 25 cycles at 94° C. for 10 seconds, 68° C. for 20 seconds, 72° C. for 40 seconds, fo lowed by a 5 minute extension at 72° C. A band of the predicted size, 690 bp, was visualized by 1% agarose gel electrophoresis, excised and the DNA was purified from the gel with a QUIAQUICK® column (Qiagen) according to the manufacturer's instructions. The DNA was digested with the restriction enzymes Bam HI and Xba I, followed by extraction and precipitated.

The excised DNA was subcloned into plasmid pZP9 which had been cut with Bam HI and Xba I. The zsig39NEE/pZP9 expression vector incorporates the TPA leader and the Glu-Glu epitope (SEQ ID NO:20) is attached at the N-terminus as a purification aid. Plasmid pZP9 (deposited at the American Type Culture Collection, 12301 Parklawn Drive, Rockville, Md., ATCC No. 98668) is a mammalian expression vector containing an expression cassette having the mouse metallothionein-1 promoter, multiple restriction sites for insertion of coding sequences, a stop codon and a human growth hormone terminator. The plasmid also has an *E. coli* origin of replication, a mammalian selectable marker expression unit having an SV40 promoter, enhancer ard origin of replication, a DHFR gene and the SV40 terminator.

30 ng of the restriction digested N-terminal Glu-Glu-zsig39 insert and 48 ng of the digested vector were ligated overnight at 16° C. One microliter of each ligation reaction was independently electrcporated into DH10B competent cells (GIBCO BRL, Gaithersburg, Md.) according to manufacturer's direction and plated onto LB plates containing 50 mg/ml ampicillin, and incubated overnight. Colonies were screened by PCR using primers ZC13006 (SEQ ID NO:23) and ZC13007 (SEQ ID NO:24). PCR screening was done at 94° C. for 4 minutes, 25 cycles of 94° C. for 30 seconds, 64° C. for 20 seconds, 72° C. for 1 minute, followed by a 10 minute extension at 72° C. Positive clones were plated on to LB Amp plates as above. The insert sequence of positive clones was verified by sequence analysis. A large scale plasmid preparation was done using a QIAGEN® Maxi prep kit (Qiagen) according to manufacturer's instructions.

Zsig39CEE/pZP9

A 744 bp PCR generated zsig39 DNA fragment was created in accordance with the procedure set forth above using ZC15609 (SEQ ID NO:25) and ZC15232 (SEQ ID NO:26) as PCR primers to add the C-terminal Glu-Glu tag and Eco RI and Bam HI restriction sites. PCR amplification was done at 94° C. for 3 minutes, 5 cycles of 94° C. for 30 seconds, 30° C. for 20 seconds, 72° C. for 1 minute, 25 cycles at 94° C. for 30 seconds, 64° C. for 20 seconds, 72° C. for 1 minute, followed by a 5 minute extension at 72° C. The purified PCR fragment was digested with the restriction enzymes Eco RI and Bam HI, followed by extraction and precipitation.

The excised zig39 DNA was subcloned into plasmid pZP9 which had been cut with Eco RI and Bam HI. The zsig39CEE/pZP9 expression vector uses the native zsig39 signal peptide and attaches the Glu-Glu tag (SEQ ID NO:20) to the C-terminal of the zsig39 polypeptide-encoding polynucleotide sequence.

Thirty four ng of the restriction digested C-terminal Glu-Glu-zsig39 insert and 48 ng of the corresponding vector were ligated into DH10B cells and positive colonies were screened as described above. Positive clones were plated on to LB Amp plates as above. The insert sequence of positive clones were verified by sequence analysis. A large scale plasmid preparation was done using a QIAGEN® Maxi prep kit (Qiagen) according to manufacturer's instructions.

EXAMPLE 5

Transfection and Expression of zsig39NEE: and CEE Polypeptides

BHK 570 cells (ATCC No. CRL-10314) were plated in 10 cm tissue culture dishes and allowed to grow to approximately 50 to 70% confluency overnight at 37° C., 5% CO$_2$, in DMEM/FBS media (DMEM, Gibco/BRL High Glucose, (Gibco BRL, Gaithersburg, Md.), 5% fetal bovine serum (Hyclone, Logan, Utah), 2 μM L-glutamine (JRH Biosciences, Lenexa, Kans.), 1 μM sodium pyruvate (Gibco BRL)). The cells were then transfected with the plasmid zsig39NEE/pZP9 (N-terminal Glu-Glu tag) or zsig39CEE/pZP9 (C-terminal Glu-Glu tag), using Lipofectamine™ (Gibco BRL), in serum free (SF) media formulation (DMEM, Gibco/BRL High Glucose, (Gibco BRL, Gaithersburg, Md.), 2 mM L-glutamine, 2 mM sodium pyruvate, 10 ug/ml transferrin, 5 µg/ml insulin, 10 µg/ml fetuin and 2 ng/ml selenium). Sixteen micrograms of zsig39NEE/pZP9 and 16 µg of zsig39CEE/pZP9 were separately diluted into 15 ml tubes to a total final volume of 640 µl SF media. In separate tubes, 35 µl of Lipofectamine™ (Gibco BRL) was mixed with 605 µl of SF medium. The Lipofectamine™ mix was added to the DNA mix and allowed to incubate approximately 30 minutes at room temperature. Five milliliters of SF media was added to the DNA:Lipofectamine™ mixture. The cells were rinsed once with 5 ml of SF media, aspirated, and the DNA:Lipofectamine™ mixture was added. The cells were incubated at 37° C. for five hours, then 6.4 ml of DMEM/10% FBS, 1% PSN media was added to the plate. The plate was incubated at 37° C. overnight and the DNA:Lipofectamine™ mixture was replaced with fresh FBS/DMEM media the next day. On day 2 post-transfection, the cells were split into the selection media (ESTEP #1 with 1 µM MTX) in 150 mm plates at 1:50, 1:100 and 1:200. The plates were refed at day 5 post-transfection with fresh selection media.

Screening Colonies

Approximately 10–12 days post-transfection, one 150 mm culture dish of methotrexate resistant colonies was chosen from each transfection, the media aspirated, the plates washed with 10 ml serum-free ESTEP 2 media (668.7 g/50L DMEM (Gibco), 5.5 g/50L pyruvic acid, sodium salt 96% (Mallinckrodt), 185.0 g/50L NaHCO$_3$ (Mallinkrodt), 5.0 mg/ml, 25 ml/50L insulin, 10.0 mg/ml and 25 ml/50 L transferrin). The wash media was aspirated and replaced with 5 ml serum-free ESTEP 2. Sterile Teflon mesh (Spectrum Medical Industries, Los Angeles, Calif.) pre-soaked in serum-free ESTEP 2 was then placed over the cells. A sterile nitrocellulose filter pre-soaked in serum-free ESTEP 2 was then placed over the mesh. Orientation marks on the nitrocellulose were transferred to the culture dish. The plates were then incubated for 5–6 hours in a 37° C., 5% CO$_2$ incubator. Following incubation, the filter was removed, and the media aspirated and replaced with DMEM/5% FBS, 1×PSN (Gibco BRL) media. The filter was then placed into a sealable bag containing 50 ml buffer (25 mM Tris, 25 mM glycine, 5 mM β-mercaptoethanol) and incubated in a 65 ° C. water bath for 10 minutes. The filters were blocked in 10% nonfat dry milk/FBS, 0.1% PBS (Sigma) for 15 minutes at room temperature on a rotating shaker. The filter was then incubated with an anti-Glu-Glu antibody-HRP conjugate at a 1:1000 dilution in 10% nonfat dry milk, 0.1% PBS, 0.1% TWEEN, overnight at 4° C. on a rotating shaker. The filter was then washed three times at room temperature in PBS plus 0.1% Tween 20, 5–15 minutes per wash. The filter was developed with ECL reagent (Amersham Corp., Arlington Heights, Ill.) according the manufacturer's directions and exposed to film (Hyperfilm ECL, Amersham) for approximately 35 seconds.

The film was aligned with the plate containing the colonies. Using the film as a guide, suitable colonies were selected. Sterile, 3 mm coloning discs (PGC Scientific Corp., Frederick, Md.) were soaked in trypsin, and placed on the colonies. Twelve colonies for each construct were transferred into 200 µl of selection medium in a 96 well plate. A series of seven, two-fold dilutions were carried out for each colony. The cells were grown for one week at 37° C. at which time the wells which received the lowest dilution of cells which are now at the optimum density were selected, trypsinized and transferred to a 12 well plate containing selection media. The 150 mm culture dish was also trypsinized and the remainder of the cells were pooled and subjected to Western Blot analysis and mycoplasma testing. The pool was frozen for storage.

The clones were expanded directly from the 12 well plate into two T-75 flasks each. One flask was kept to continue cell growth, the second flask was grown in serum-free ESTEP 2 which was harvested for Western Blot analysis. Clones of each of the expressior constructs, based on Western blot analysis, were selected, pooled and transferred to large scale culture.

EXAMPLE 6

Large Scale Mammalian Expression of zsig39CEE and zsig39NEE

One T-162 flask, containing confluent cells expressing zsig39CEE and one containing zsig39NEE obtained from the expression procedure described above, were expanded into six T-162 flasks each. One of the six resulting flasks was used to freeze down four cryovials, and the other five flasks were used to generate a Nunc cell factory.

The cells from the five T-162 flasks of zsig39CEE and zsig39NEE were used to independently seed two Nunc cell factories (10 layers, commercially available from VWR). Briefly, the cells from the T-162 flasks described above were detached using trypsin, pooled, and added to 1.5 liters ESTEP1 media. (668.7 g/50L DMEM (Gibco), 5.5 g/50L pyruvic acid, sodium salt 96% (Mallinckrodt), 185.0 g/50L NaHCO$_3$ (Mallinckrodt), 5.0 mg/ml and 25 ml/50L insulin (JRH Biosciences), 10.0 mg/ml and 25 ml/50L transferrin (JRH Biosciences), 2.5L/50L fetal bovine serum (characterized) (Hyclone), 1 µM MTX, with pH adjusted to 7.05+/−0.05) prewarmed to 37° C. The media containing the cells was then poured into the Nunc cell factories via a funnel. The cell factories were placed in a 37° C./5.0% CO$_2$ incubator.

At 80–100% confluence, a visual contamination test (phenol red color change) was performed on the contents of the Nunc cell factories. Since no contamination was observed, supernatant from the confluent factories was poured into a small harvest container, sampled and discarded. The adherent cells were then washed once with 400 ml PBS. To detach the cells from the factories, 100 mls of trypsin was added to each and removed and the cells were then incubated for 2 or 5 minutes in the residual trypsin. The cells were collected in two, 200 ml washes with ESTEP1 media. To each of ten ESTEP1 media-containing bottles (1.5 liters each, at 37° C.) was added 40 mls of collected cells. One 1.5 liter bottle was then used to fill one Nunc factory. Each cell factory was placed in a 37° C./5.0% CO$_2$ incubator.

At 80–90% confluence, a visual contamination test (phenol red color change) was performed on the Nunc cell factories. Since no contamination was observed, supernatant from the confluent factories was poured into a small harvest container, sampled and discarded. Cells were then washed once with 400 ml PBS. 1.5 liters of ESTEP2 media (668.7 g/50L DMEM (Gibco), 5.5 g/50L pyruvic acid, sodium salt 96% (Mallinckrodt), 185.0 g/50L NaHCO$_3$ (Mallinckrodt), 5.0 mg/ml, 25 ml/50L insulin, 10.0 mg/ml and 25 ml/50L transferrin) was added to each Nunc cell factory. The cell factories were incubated at 37° C./5.0% CO$_2$.

At approximately 48 hours a visual contamination test (phenol red color change) was performed on the Nunc cell factories. Supernatant from each factory was poured into small harvest containers. Fresh serum-free media (1.5 liters)

was poured into each Nunc cell factory, and the factories were incubated at 37° C./5.0% $CO_2$. One ml of supernatant harvest for each construct was transferred to a microscope slide, and subjected to microscopic analysis for contamination. The contents of the small harvest containers for each construct were pooled and immediately filtered. A second harvest was then performed, substantially as described above at 48 hours and the cell factories were discarded thereafter. An aseptically assembled filter train apparatus was used for aseptic filtration of the harvest supernatant (conditioned media). Assembly was as follows: tubing was wire-tied to an Opti-Cap filter (Millipore Corp., Bedford, Mass.) and a Gelman Supercap 50 filter (Gelman Sciences, Ann Arbor, Mich.). The Supercap 50 filter was also attached to a sterile capped container located in a hood; tubing located upstream of the Millipore Opti-cap filter was inserted into a peristaltic pump; and the free end of the tubing was placed in the large harvest container. The peristaltic pump was run between 200 and 300 rpm, until all of the conditioned media passed through the 0.22 $\mu$m final filter into a sterile collection container. The filtrate was placed in a 4° C. cold room pending purification. The media samples saved from the various time points were concentrated 10× with a Millipore 5 kDA cut off concentrator (Millipore Corp., Bedford, Mass.) according to manufacturer's direction and subjected to Western Blot analysis. Variation in the mobility of the standards is likely responsible for the apparent size difference between the two preparations.

Zsiq39CEE:

5 T-162 Flasks=>0.125 mg/L, 28 kDa;

1 Factory, FBS=>0.125 mg/L, 28 kDa;

10 Factories, FBS=>0.125 mg/L, 28 kDa;

10 Factories (#1), SF=>0.125 mg/L, 28 kDa; and

10 Factories (#2), SF=>0.125 mg/L, 28 kDa

Zsiq39NEE:

5 T-162 Flasks=0.14 mg/L, 38 kDa;

1 Factory, FBS=1.39 mg/L, 38 kDa;

10 Factories, FBS=0.14 mg/L, 38 kDa;

10 Factories (#1), SF=1.39 mg/L, 38 kDa; and

10 Factories (#2), SF=1.39 mg/L, 38 kDa.

EXAMPLE 7

Purification Conditions for zsig39 NEE and CEE

Unless otherwise noted, all operations were carried out at 4° C. The following procedure was used for purifying zsig39 containing N-terminal or C-terminal Glu-Glu (EE) tags described above. A total of 25 liters of conditioned media from baby hamster kidney (BHK) cells was sequentially sterile filtered through a 4 inch, 0.2 mM Millipore (Bedford, Mass.) OptiCap capsule filter and a 0.2 mM Gelman (Ann Arbor, Mich.) Supercap 50. The material was then concentrated to about 1.3 liters using a Millipore ProFlux A30 tangential flow concentrator fitted with a 3000 kDa cutoff Amicon (Bedford, Mass.) S10Y3 membrane. The concentrated material was again sterile-filtered with the Gelman filter as described above. A mixture of protease inhibitors was added to the concentrated conditioned media to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). A 25.0 ml sample of anti-EE Sepharose, prepared as described below, was added to the sample for batch adsorption and the mixture was gently agitated on a Wheaton (Millville, N.J.) roller culture apparatus for 18.0 h at 4° C.

The mixture was then poured into a 5.0×20.0 cm Econo-Column (Bio-Rad, Laboratories, Hercules, Calif.) and the gel was washed with 30 column volumes of phosphate buffered saline (PBS). The unretained flow-through fraction was discarded. Once the absorbance of the effluent at 280 nM was less than 0.05, flow through the column was reduced to zero and the anti-EE Sepharose gel was washed batchwise with 2.0 column volumes of PBS containing 0.4 mg/ml of EE peptide (AnaSpec, San Jose, Calif.). The peptide used has the sequence Glu-Tyr-Met-Pro-Val-Asp (SEQ ID NO:27). After 1.0 h at 4° C., flow was resumed and the eluted protein was collected. This fraction was referred to as the peptide elution. The anti-EE Sepharose gel was then washed with 2.0 column volumes of 0.1 M glycine, pH 2.5, and the glycine wash was collected separately. The pH of the glycine-eluted fraction was adjusted to 7.0 by the addition of a small volume of 10×PBS and stored at 4° C. for future analysis if needed.

The peptide elution was concentrated to 5.0 ml using a 15,000 molecular weight cutoff membrane concentrator (Millipore, Bedford, Mass.) according to the manufacturer's instructions. The concentrated peptide elution was separated from free peptide by chromatography on a 1.5×50 cm Sephadex G-50 (Pharmacia, Piscataway, N.J.) column equilibrated in PBS at a flow rate of 1.0 ml/min using a BioCad Sprint HPLC (PerSeptive BioSystems, Framingham, Mass.). Two ml fractions were collected and the absorbance at 280 nM was monitored. The first peak of material absorbing at 280 nM and eluting near the void volume of the column was collected. This fraction was pure zsig39 NEE or zsig39 CEE. The pure material was concentrated as described above, analyzed by SDS-PAGE and Western blotting with anti-Glu-Glu antibodies, and samples were taken for amino acid analysis and N-terminal sequencing. The remainder of the sample was aliquoted, and stored at −80° C. according to our standard procedures. The protein concentration of the purified zsig39 NEE was 0.65 mg/ml. The protein concentration of zsig39 CEE was 0.3 mg/ml.

Electrophoresis of zsig39 NEE on SDS-PAGE gels in the absence of reducing agents showed two bands, present in about equimolar amounts, on Coomassie Blue-stained gels of apparent molecular weights ~50,000 and ~29,000. On western blots these bands showed cross-reactivity with anti-EE antibodies. Three other bands of apparent molecular weights ~150,000, ~80,000, and ~60,000 were also observed on western blots under these conditions. In the presence of reducing agent, the only band observed on Coomassie Blue stained gels migrated with an apparent molecular weight of 30,000. The intensity of this band was increased relative to either band observed on non-reducing gels. The 30,000 kDa band also showed cross-reactivity with anti-EE antibodies on western blots and was the only cross-reactive protein present. In addition, the intensity of this band was increased relative to the intensity of the band under non-reducing conditions. Virtually identical results were obtained for zsig39 CEE by SDS-PAGE and western blotting with anti-EE antibodies.

Preparation of anti-EE Sepharose

A 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma Co.) and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce), dissolved in TEA, was added to a final concentration of 36 mg/ml of gel. The gel was rocked at room temperature for 45 min and the liquid was removed using the filter unit as described above. Nonspecific sites on the gel were then blocked by incubating for 10 min at room temperature with 5 volumes of 20 mM ethanolamine in 200 mM TEA. The gel was washed with 5 volumes of PBS containing 0.02% sodium azide and stored in this solution at 4° C.

EXAMPLE 8

Construction of zsig39 Amino Terminal Glu-Gl-u Tagged and Carboxy Terminal Glu-Glu Tagged Yeast Expression Vectors Expression of zsig39 in *Pichia methanolica* utilizes the expression system described in co-assigned WIPO publication WO 97/17450. An expression plasmid containing all or part of a polynucleotide encoding zsig39 is constructed via homologous recombination. An expression vector was built from pCZR204 to express C-terminal Glu-Glu-tagged (CEE) zsig39 polypeptides. The pCZR204 vector contains the AUG1 promoter, followed by the αFpp leader sequence, followed by a blunt-ended Sma I restriction site, a carboxy-terminal peptide tag (Glu-Glu), a translational STOP codon, followed by the AUG1 terminator, the ADE2 selectable marker, and finally the AUG1 3' untranslated region. Also included in this vector are the URA3 and CEN-ARS sequences required for selection and replication in *S. cerevisiae*, and the AmpR and colE1 ori sequences required for selection and replication in *E. coli*. A second expression vector was built from zCZR204 to express a N-terminal Glu-Glu-tagged (NEE) zsig39 polypeptides. The zCZR204 expression vector is as described above, having an amino terminal Glu-Glu tag. The zsig39 sequence inserted into these vectors begins at residue 19 (Leu) of the zsig39 amino acid sequence (SEQ ID NO:2).

For each construct two linkers are prepared, and along with zsig39, were homologously recombined into the yeast expression vectors described above. The untagged N-terminal linker (SEQ ID NO:28) spans 70 base pairs of the alpha factor prepro (aFpp) coding sequence on one end and joins it to the 70 base pairs of the amino-terminus coding sequence from the mature zsig39 sequence on the other. The NEE-tagged linker (SEQ ID NO:29) joins Glu-Glu tag (SEQ ID NO:20) between the aFpp coding sequence and the zsig39 sequence. The untagged C-terminal linker (SEQ ID NO:30) spans about 70 base pairs of carboxy terminus coding sequence of the zsig39 on one end with 70 base pairs of AUG1 terminator sequence. The CEE-tagged linker (SEQ ID NO:31) inserts the Glu-Glu tag (SEQ ID NO:20) between the C-terminal end of zsig39 and the AUG1 terminator region.

Construction of the NEE-tagged-Zsiq39 Plasmid

An NEE-tagged-zsig39 plasmid was made by homologously recombining 100 ng of the SmaI digested pCZR204 acceptor vector, 1 μg of Eco RI-Bam HI zsig39 cDNA donor fragment, 1 μgNEE-tagged-zsig39 linker (SEQ ID NO:29) and 1 μg of C-terminal untagged linker (SEQ ID NO:30) in *S. cerevisiae*.

The NEE-zsig39 linker was synthesized by a PCR reaction. To a final reaction volume of 100 μl was added 1 pmol each of linkers, ZC13731 (SEQ ID NO:32) and ZC15268 (SEQ ID NO:33), and 100 pmol of each primer ZC13497 (SEQ ID NO:34) and ZC15274 (SEQ ID NO:35), 10 μl of 10×PCR buffer (Boehringer Mannheim), 1 μl Pwo Polymerase (Boehringer Mannheim), 10 μl of 0.25 mM nucleotide triphosphate mix (Perkin Elmer) and dH$_2$O. The PCR reaction was run 10 cycles at 30 seconds at 94° C., 1 minute at 50° C. and 1 minute at 72° C., concluded with a 6 minute extension at 72°. The resulting 144 bp double stranded, NEE-tagged linker is disclosed in SEQ ID NO:29.

The C-terminal untagged zsig39 linker was made via a PCR reaction as described using oligonucleotides ZC15273 (SEQ ID NO:36), ZC15724 (SEQ ID NO:37), ZC15223 (SEQ ID NO:38) and ZC13734 (SEQ ID NO:39). The resulting 147 bp double stranded, C-terminal untagged linker is disclosed in SEQ ID NO:30.

Construction of the CEE-zsig39 Plasmid

A CEE-zsig39 plasmid was made by homologously recombining 100 ng of Sma I digested pCZR204 acceptor vector, the 1 μg of Eco RI-Bam HI zsig39 cDNA donor fragment, 1 μg of N-terminal untagged zsig39 linker (SEQ ID NO:28) and 1 μg of CEE-tagged linker (SEQ ID NO:31) in a *S. cerevisiae*.

The N-terminal untagged zsig39 linker was made via a PCR reaction as described above using oligonucleotides ZC14822 (SEQ ID NO:40), ZC14821 (SEQ ID NO:41), ZC15269 (SEQ ID NO:42) and ZC15274 (SEQ ID NO:43). The resulting 144 bp double stranded, N-terminal untagged linker is disclosed in SEQ ID NO:28.

The CEE-tagged linker was made via a PCR reaction as described above using ZC15273 (SEQ ID NO:44), ZC15267 (SEQ ID NO:45), ZC14819 (SEQ ID NO:49) and ZC14820 (SEQ ID NO:47). The resulting approximately 144 bp double stranded, CEE-tagged linker is disclosed in SEQ ID NO:31.

One hundred microliters of competent yeast cells (*S. cerevisiae*) was independently combined with 10 μl of the various DNA mixtures from above and transferred to a 0.2 cm electroporation cuvette. The yeast/DNA mixtures were electropulsed at 0.75 kV (5 kV/cm), ∞ ohms, 25 μF. To each cuvette was added 600 μl of 1.2 M sorbitol and the yeast was plated in two 300 μl aliquots onto two URA D plates and incubated at 30° C.

After about 48 hours the Ura$^+$ yeast transformants from a single plate were resuspended in 2.5 ml H$_2$O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 200 μl phenol-chloroform, vortexed for 1 minute intervals two or three times, followed by a 5 minute spin in a Eppendorf centrifuge as maximum speed. Three hundred microliters of the aqueous phase was transferred to a fresh tube and the DNA precipitated with 600 μl ethanol (EtOH), followed by centrifugation for 10 minutes at 40° C. The DNA pellet was resuspended in 100 μl H$_2$O.

Transformation of electrocompetent *E. coli* cells (DH10B, Gibco BRL) was done with 1 μl yeast DNA prep and 50 μl of DH10B cells. The cells were electropulsed at 2.0 kv, 25 μF and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) was plated in 250 μl aliquots on four LB AMP plates (LB broth (Lennox), 1.8% Bacto™ Agar (Difco), 100 mg/L Ampicillin).

Individual clones harboring the correct expression construct for NEE and CEE tagged zsig39 constructs were identified by sequence analysis to verify the presence of the zsig39 insert and to confirm that the various DNA sequences had been joined correctly to one another. The insert of positive clones were subjected to sequence analysis. Larger scale plasmid DNA was isolated using the Qiagen Maxi kit (Qiagen) according to manufacturer's instruction and the DNA was digested with Not I to liberate the Pichia-Zsig39 expression cassette from the vector backbone. The Not I-restriction digested DNA fragment was then transformed into the *Pichia methanolica* expression host, PMAD16. This was done by mixing 100 µl of prepared competent PMAD16 cells with 10 µg of Not I restriction digested zsig39 and transferred to a 0.2 cm electroporation cuvette. The yeast/ DNA mixture was electropulsed at 0.75 kV, 25 µF, infinite ohms. To the cuvette was added 1 ml of 1×Yeast Nitrogen Base and 500 µl aliquots were plated onto two ADE DS (0.056% -Ade -Trp -Thr powder, 0.67% yeast nitrogen base without amino acids, 2% D-glucose, 0.5% 200×tryptophan, threonine solution, and 18.22% D-sorbitol) plates for selection and incubated at 30° C. Clones were picked and screened via Western blot for high-level zsig39 expression. The resulting NEE-tagged-zsig39 plasmid containing yeast cells were designated PMAD16::pCZR206.14.51 and 14.61 and the CEE-tagged-zsig39 plasmid containing yeast cells were designated PMAD16::pCZR209#1 and #2. The clones were then subjected to fermentation.

EXAMPLE 9

Purification of zsig39CEE from *Pichia methanolica* Conditioned Medium

Unless otherwise noted, all operations were carried out at 4° C. A mixture of protease inhibitors was added to a 3000 ml sample of conditioned media from Pichia cultures to final concentrations of 2.5 mM ethylenediaminetetraacetic acid (EDTA, Sigma Chemical Co.), 0.001 mM leupeptin (Boehringer-Mannheim), 0.001 mM pepstatin (Boehringer-Mannheim) and 0.4 mM Pefabloc (Boehringer-Mannheim). The pH of the media was adjusted to 7.2 with a concentrated solution of NaOH (Sigma Chemical Co.) following the addition of potassium phosphate (Sigma Chemical Co.) to a final concentration of 0.05M. The sample was centrifuged at 18,000×g for 30 min at 4° C. in a Beckman JLA-10.5 rotor (Beckman Instruments) in a Beckman Avanti J25I centrifuge (Beckman Instruments) to remove cell debris. To the supernatant fraction was added a 50.0 ml sample of anti-EE Sepharose, prepared as described above, and the mixture was gently agitated on a Wheaton (Millville, N.J.) roLler culture apparatus for 18.0 h at 4° C. The mixture was then processed as described above for zsig39CEE from BHK cells. The pure material was concentrated as described above, analyzed by SDS-PAGE and Western blotting with anti-EE antibodies, and samples were taken for amino acid analysis and N-terminal sequencing. The remainder of the sample was aliquoted, and stored at −80° C. according to our standard procedures.

On Coomassie Blue-stained SDS-PAGE gels, the preparation contained two major bands of apparent molecular weights 23,000 and 28,000 and two minor components of 21,000 and 45,000. The mobility of these bands was the same in the presence and absence of reducing agents. The only band visible on western blots with anti-EE antibodies in the absence of reducing agents was a protein of apparent molecular weight 150,000 (probably IgG that eluted from the anti EE sepharose column). Western blotting with anti-EE antibodies in the presence of reducing agents, in contrast, showed three bands of apparent molecular weights 28,000, 24,000, and 23,000. The concentration of zsig39CEE from *Pichia methanolica* was 0.35 mg/ml.

EXAMPLE 10

Zsig39 Antibodies

A polyclonal antibody was prepared by immunizing two female New Zealand white rabbits with the full length zsig39 polypeptide (SEQ ID NO:2). The polypeptide was derived from purified BHK expressed material described above. The polypeptide was conjugated to the carrier protein keyhole limpet hemc,cyanin (KLH) with gluteraldehyde. The rabbits were each given an initial intraperitoneal (ip) injection of 200 µg of peptide in Complete Freund's Adjuvant followed by booster ip injections of 100 µg peptide in Incomplete Freund's Adjuvant every three weeks. Seven to ten days after the administration of the third booster injection, the animals were bled and the serum was collected. The animals were then boosted and bled every three weeks.

The zsig39 specific antibody was purified from the serum using a Protein A Sepharose. The zsig39 antibody can be characterized by an ELISA titer check using the polypeptide of SEQ ID NO:2 as an antibody target.

EXAMPLE 11

In vivo Administration of zsig39 Via Adenoviral Delivery

Twenty four male and 24 female C57B16/J mice, approximately 12 weeks old (Jackson Labs, Bar Harbor, Me.) were weighed, body temperature was measured and food intake monitored daily for four days prior to injection (days -4 to -1). On day 0, the mice were divided into three groups and received 0.1 ml virus (AdV-empty $1.8 \times 10^{11}$ virus particles/ 0.1 ml or AdV-zsig39-CEE $5 \times 10^{11}$ virus particles/0.1 ml) by intravenous tail vein injection, or no injection at all. Injection should result in infection of the host's liver and expression of virally delivered gene should commence within 24 hours and continue for 1 to 4 weeks. Three groups of mice were tested. Group 1, untreated, n=8 each male and female. Group 2, AdV-Empty (empty virus), n=8 each male and female. Group 3, AdV-zsig39 CEE, n=8 each male and female. Production of adenovirus containing zsig39CEE was done according to the procedure of Becker et al., *Meth. Cell Biol.* 43:161–89, 1994 using commercially available vectors.

The animals' body temperatures, weights and the weight of food ingested was monitored during the three week study. No difference was found between the groups.

On day 21 the female mice were euthanized and sacrificed by cervical dislocation, and on day 22 the males were. The animals were exsanguinated and tissues harvested for necropsy.

The standard serum chemistry panel was done at the time of sacrifice. Liver, kidney and metabolic parameters were all within normal ranges. Total free fatty acids were assayed on the remaining serum from each animal. A statistically significant difference in serum Free Fatty Acid levels was seen between both female and male mice (p<0.05% for both) receiving empty virus and those receiving zsig39 encoding virus by Dunn's Multiple Comparisons Test. The zsig39 mice had lower levels. Liver, spleen, kidney, thymus, heart and brain were weighed after removal. These tissues and femurs were saved for histology. Histopathological analysis of femoral metaphyseal bone marrow revealed a difference between the treatment groups. The mean % of fat score from the metaphyseal bone marrow of female zsig39 mice was significantly greater (p<0.05% by Dunn's Multiple Comparisons Test) than that of the female mice receiving the empty adenovirus. No significant observations were made on the other tissues examined.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide selected from the group consisting of:

a) a polypeptide comprising a sequence of amino acid residues from amino acid residue 30 to amino acid residue 95 of SEQ ID NO:2;

b) a polypeptide comprising a sequence of amino acid residues from amino acid residue 30 to amino acid residue 96 of SEQ ID NO:2; and c) a polypeptide comprising a sequence of amino acid residues from amino acid residue 30 to 97 of SEQ ID NO:2;

d) a polypeptide comprising a sequence of amino acid residues from amino acid residue 30 to amino acid residue 98 of SEQ ID NO:2;

e) a polypeptide comprising a sequence of amino acid residues from amino acid residue 98 to amino acid residue 243 of SEQ ID NO:2;

f) a polypeptide comprising a sequence of amino acid residues from amino acid residue 99 to amino acid residue 243 of SEQ ID NO:2; and g) a polypeptide comprising a sequence of amino acid residues from amino acid residue 30 to amino acid residue 243 of SEQ ID NO:2.

2. An isolated polypeptide according to claim 1, covalently linked amino terminally or carboxy terminally to a moiety selected from the group consisting of affinity tags, toxins, radionucleotides, enzymes and fluorophores.

3. A pharmaceutical composition comprising a polypeptide according to claim 1, in combination with a pharmaceutically acceptable vehicle.

* * * * *

SEQUENCE LISTING

<160> NUMBER OF SEQ ID NOS: 47

<210> SEQ ID NO 1
<211> LENGTH: 1347
<212> TYPE: DNA
<213> ORGANISM: Homo sapiens
<220> FEATURE:
<221> NAME/KEY: CDS
<222> LOCATION: (198)...(926)

<400> SEQUENCE: 1

```
gaattcggct cgagagggag cgaaccagga ctggggtgac ggcagggcag ggggcgcctg      60
gccggggaga agcgcggggg ctggagcacc accaactgga gggtccggag tagcgagcgc     120
cccgaaggag gccatcgggg agccgggagg ggggactgcg agaggacccc ggcgtccggg     180
ctcccggtgc cagcgct atg agg cca ctc ctc gtc ctg ctg ctc ctg ggc       230
                    Met Arg Pro Leu Leu Val Leu Leu Leu Leu Gly
                     1               5                  10 ctg gcg gcc ggc tcg ccc cca ctg gac gac aac aag atc ccc agc ctc       278
Leu Ala Ala Gly Ser Pro Pro Leu Asp Asp Asn Lys Ile Pro Ser Leu
             15                  20                  25 tgc ccg ggg cac ccc ggc ctt cca ggc acg ccg ggc cac cat ggc agc       326
Cys Pro Gly His Pro Gly Leu Pro Gly Thr Pro Gly His His Gly Ser
         30                  35                  40 cag ggc ttg ccg ggc cgc gat ggc cgc gac ggc cgc gac ggc gcg ccc       374
Gln Gly Leu Pro Gly Arg Asp Gly Arg Asp Gly Arg Asp Gly Ala Pro
     45                  50                  55 ggg gct ccg gga gag aaa ggc gag ggc ggg agg ccg gga ctg ccg gga       422
Gly Ala Pro Gly Glu Lys Gly Glu Gly Gly Arg Pro Gly Leu Pro Gly
 60                  65                  70                  75 cct cga ggg gac ccc ggg ccg cga gga gag gcg gga ccc gcg ggg ccc       470
Pro Arg Gly Asp Pro Gly Pro Arg Gly Glu Ala Gly Pro Ala Gly Pro
                 80                  85                  90 acc ggg cct gcc ggg gag tgc tcg gtg cct ccg cga tcc gcc ttc agc       518
Thr Gly Pro Ala Gly Glu Cys Ser Val Pro Pro Arg Ser Ala Phe Ser
             95                 100                 105 gcc aag cgc tcc gag agc cgg gtg cct ccg cct tct gac gca ccc ttg       566
Ala Lys Arg Ser Glu Ser Arg Val Pro Pro Pro Ser Asp Ala Pro Leu
        110                 115                 120 ccc ttc gac cgc gtg ctg gtg aac gag cag gga cat tac gac gcc gtc       614
Pro Phe Asp Arg Val Leu Val Asn Glu Gln Gly His Tyr Asp Ala Val
    125                 130                 135 acc ggc aag ttc acc tgc cag gtg cct ggg gtc tac tac ttc gcc gtc       662
Thr Gly Lys Phe Thr Cys Gln Val Pro Gly Val Tyr Tyr Phe Ala Val
140                 145                 150                 155 cat gcc acc gtc tac cgg gcc agc ctg cag ttt gat ctg gtg aag aat       710
His Ala Thr Val Tyr Arg Ala Ser Leu Gln Phe Asp Leu Val Lys Asn
                160                 165                 170
```

```
ggc gaa tcc att gcc tct ttc ttc cag ttt ttc ggg ggg tgg ccc aag     758
Gly Glu Ser Ile Ala Ser Phe Phe Gln Phe Phe Gly Gly Trp Pro Lys
        175                 180                 185 cca gcc tcg ctc tcg ggg ggg gcc atg gtg agg ctg gag cct gag gac     806
Pro Ala Ser Leu Ser Gly Gly Ala Met Val Arg Leu Glu Pro Glu Asp
        190                 195                 200 caa gtg tgg gtg cag gtg ggt gtg ggt gac tac att ggc atc tat gcc     854
Gln Val Trp Val Gln Val Gly Val Gly Asp Tyr Ile Gly Ile Tyr Ala
        205                 210                 215 agc atc aag aca gac agc acc ttc tcc gga ttt ctg gtg tac tcc gac     902
Ser Ile Lys Thr Asp Ser Thr Phe Ser Gly Phe Leu Val Tyr Ser Asp
220                 225                 230                 235 tgg cac agc tcc cca gtc ttt gct tagtgccccac tgcaaagtga gctcatgctc   956
Trp His Ser Ser Pro Val Phe Ala
                240 tcactcctag aaggagggtg tgaggctgac aaccaggtca tccaggaggg ctggcccccc   1016 tggaatattg tgaatgacta gggaggtggg gtagagcact ctccgtcctg ctgctggcaa   1076 ggaatgggaa cagtggctgt ctgcgatcag gtctggcagc atggggcagt ggctggattt   1136 ctgcccaaga ccagaggagt gtgctgtgct ggcaagtgta agtcccccag ttgctctggt   1196 ccaggagccc acggtgggt gctctcttcc tggtcctctg cttctctgga tcctccccac    1256 cccctcctgc tcctggggcc ggccctttc tcagagatca ctcaataaac ctaagaaccc    1316 tcaaaaaaaa aaaaaaaaaa agggcggccg c                                  1347

<210> SEQ ID NO 2
<211> LENGTH: 243
<212> TYPE: PRT
<213> ORGANISM: Homo sapiens

<400> SEQUENCE: 2

Met Arg Pro Leu Leu Val Leu Leu Leu Gly Leu Ala Ala Gly Ser
1               5                   10                  15

Pro Pro Leu Asp Asp Asn Lys Ile Pro Ser Leu Cys Pro Gly His Pro
            20                  25                  30

Gly Leu Pro Gly Thr Pro Gly His His Gly Ser Gln Gly Leu Pro Gly
        35                  40                  45

Arg Asp Gly Arg Asp Gly Arg Asp Gly Ala Pro Gly Ala Pro Gly Glu
    50                  55                  60

Lys Gly Glu Gly Gly Arg Pro Gly Leu Pro Gly Pro Arg Gly Asp Pro
65                  70                  75                  80

Gly Pro Arg Gly Glu Ala Gly Pro Ala Gly Pro Thr Gly Pro Ala Gly
                85                  90                  95

Glu Cys Ser Val Pro Pro Arg Ser Ala Phe Ser Ala Lys Arg Ser Glu
            100                 105                 110

Ser Arg Val Pro Pro Pro Ser Asp Ala Pro Leu Pro Phe Asp Arg Val
        115                 120                 125

Leu Val Asn Glu Gln Gly His Tyr Asp Ala Val Thr Gly Lys Phe Thr
    130                 135                 140

Cys Gln Val Pro Gly Val Tyr Tyr Phe Ala Val His Ala Thr Val Tyr
145                 150                 155                 160

Arg Ala Ser Leu Gln Phe Asp Leu Val Lys Asn Gly Glu Ser Ile Ala
                165                 170                 175

Ser Phe Phe Gln Phe Phe Gly Gly Trp Pro Lys Pro Ala Ser Leu Ser
            180                 185                 190

Gly Gly Ala Met Val Arg Leu Glu Pro Glu Asp Gln Val Trp Val Gln
```

```
                       195                 200                 205
Val Gly Val Gly Asp Tyr Ile Gly Ile Tyr Ala Ser Ile Lys Thr Asp
        210                 215                 220
Ser Thr Phe Ser Gly Phe Leu Val Tyr Ser Asp Trp His Ser Ser Pro
225                 230                 235                 240
Val Phe Ala

<210> SEQ ID NO 3
<211> LENGTH: 244
<212> TYPE: PRT
<213> ORGANISM: Homo sapiens

<400> SEQUENCE: 3

Met Leu Leu Gly Ala Val Leu Leu Leu Ala Leu Pro Gly His
 1               5                  10                  15

Asp Gln Glu Thr Thr Thr Gln Gly Pro Gly Val Leu Leu Pro Leu Pro
                20                  25                  30

Lys Gly Ala Cys Thr Gly Trp Met Ala Gly Ile Pro Gly His Pro Gly
            35                  40                  45

His Asn Gly Ala Pro Gly Arg Asp Gly Arg Asp Gly Thr Pro Gly Glu
        50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
                100                 105                 110

Ser Ala Phe Ser Val Gly Leu Glu Thr Tyr Val Thr Ile Pro Asn Met
            115                 120                 125

Pro Ile Arg Phe Thr Lys Ile Phe Tyr Asn Gln Gln Asn His Tyr Asp
        130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 4
<211> LENGTH: 245
<212> TYPE: PRT
<213> ORGANISM: Homo sapiens

<400> SEQUENCE: 4

Met Glu Gly Pro Arg Gly Trp Leu Val Leu Cys Val Leu Ala Ile Ser
 1               5                  10                  15

Leu Ala Ser Met Val Thr Glu Asp Leu Cys Arg Ala Pro Asp Gly Lys
                20                  25                  30
```

```
Lys Gly Glu Ala Gly Arg Pro Gly Arg Gly Arg Pro Gly Leu Lys
             35                  40                  45

Gly Glu Gln Gly Glu Pro Gly Ala Pro Gly Ile Arg Thr Gly Ile Gln
 50                  55                  60

Gly Leu Lys Gly Asp Gln Gly Glu Pro Gly Pro Ser Gly Asn Pro Gly
 65                  70                  75                  80

Lys Val Gly Tyr Pro Gly Pro Ser Gly Pro Leu Gly Ala Arg Gly Ile
                 85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
            115                 120                 125

Asn Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
            195                 200                 205

Leu Gln Gln Gly Asp Gln Val Trp Val Glu Lys Asp Pro Lys Lys Gly
210                 215                 220

His Ile Tyr Gln Gly Ser Glu Ala Asp Ser Val Phe Ser Gly Phe Leu
225                 230                 235                 240

Ile Phe Pro Ser Ala
                245

<210> SEQ ID NO 5
<211> LENGTH: 215
<212> TYPE: PRT
<213> ORGANISM: Tamias sibricus

<400> SEQUENCE: 5

Met Pro Ala Gln Arg Gly Gly Ala Leu Ser Met Gly Ala Ala Gly Phe
  1               5                  10                  15

Trp Ile Leu Val Leu Ser Ile Thr Ser Ala Leu Ala Asp Ser Asn Asn
                 20                  25                  30

Gln Gly Asn Ser Glu Pro Cys Gly Pro Pro Gly Pro Pro Gly Pro Pro
             35                  40                  45

Gly Ile Pro Gly Phe Pro Gly Ala Pro Gly Ala Leu Gly Pro Pro Gly
 50                  55                  60

Pro Pro Gly Val Pro Gly Ile Pro Gly Pro Gln Gly Pro Pro Gly Asp
 65                  70                  75                  80

Val Glu Lys Cys Ser Ser Arg Pro Lys Ser Ala Phe Ala Val Lys Leu
                 85                  90                  95

Ser Glu Arg Pro Pro Glu Pro Phe Gln Pro Ile Val Phe Lys Glu Ala
            100                 105                 110

Leu Tyr Asn Gln Glu Gly His Phe Asn Met Ala Thr Gly Glu Phe Ser
            115                 120                 125

Cys Val Leu Pro Gly Val Tyr Asn Phe Gly Phe Asp Ile Arg Leu Phe
            130                 135                 140

Gln Ser Ser Val Lys Ile Arg Leu Met Arg Asp Gly Ile Gln Val Arg
145                 150                 155                 160
```

```
Glu Lys Glu Ala Gln Ala Asn Asp Ser Tyr Lys His Ala Met Gly Ser
                165                 170                 175

Val Ile Met Ala Leu Gly Lys Gly Asp Lys Val Trp Leu Glu Ser Lys
            180                 185                 190

Leu Lys Gly Thr Glu Ser Glu Lys Gly Ile Thr His Ile Val Phe Phe
        195                 200                 205

Gly Tyr Leu Leu Tyr Gly Lys
    210                 215

<210> SEQ ID NO 6
<211> LENGTH: 236
<212> TYPE: PRT
<213> ORGANISM: Tamias sibricus

<400> SEQUENCE: 6

Met Tyr Glu Ala Gly Lys Arg Ala Ser Phe Met Gly Gly Ala Gly Ile
1               5                   10                  15

Trp Ile Leu Ala Leu Ser Val Leu Met His Val Val Cys Ser Met Tyr
            20                  25                  30

Glu Ala Gly Lys Arg Ala Ser Phe Met Gly Gly Ala Gly Ile Trp Ile
        35                  40                  45

Leu Ala Leu Ser Val Leu Met His Val Val Cys Ser Asn Val Pro Gly
    50                  55                  60

Pro Gln Gly Pro Pro Gly Met Arg Gly Pro Pro Gly Thr Pro Gly Lys
65                  70                  75                  80

Pro Gly Pro Pro Gly Trp Asn Gly Phe Pro Gly Leu Pro Gly Pro Pro
                85                  90                  95

Gly Pro Pro Gly Met Thr Val Asn Cys His Ser Lys Gly Thr Ser Ala
            100                 105                 110

Phe Ala Val Lys Ala Asn Glu Leu Pro Pro Ala Pro Ser Gln Pro Val
        115                 120                 125

Ile Phe Lys Glu Ala Leu His Asp Ala Gln Gly His Phe Asp Leu Ala
    130                 135                 140

Thr Gly Val Phe Thr Cys Pro Val Pro Gly Leu Tyr Gln Phe Gly Phe
145                 150                 155                 160

His Ile Glu Ala Val Gln Arg Ala Val Lys Val Ser Leu Met Arg Asn
                165                 170                 175

Gly Thr Gln Val Met Glu Arg Glu Ala Glu Ala Gln Asp Gly Tyr Glu
            180                 185                 190

His Ile Ser Gly Thr Ala Ile Leu Gln Leu Gly Met Glu Asp Arg Val
        195                 200                 205

Trp Leu Glu Asn Lys Leu Ser Gln Thr Asp Leu Glu Arg Gly Thr Val
    210                 215                 220

Gln Ala Val Phe Ser Gly Phe Leu Ile His Glu Asn
225                 230                 235

<210> SEQ ID NO 7
<211> LENGTH: 222
<212> TYPE: PRT
<213> ORGANISM: Rattus norvegicus

<400> SEQUENCE: 7

Met Pro Ala Pro Gly Arg Gly Pro Arg Gly Pro Leu Leu Ser Met Pro
1               5                   10                  15

Gly Arg Arg Gly Ala Leu Arg Glu Pro Ala Asp Phe Gly Ser Ser Leu
            20                  25                  30
```

Gly Ala Ala Leu Ala Leu Leu Leu Leu Leu Pro Ala Cys Cys Pro
            35                  40                  45

Val Lys Met Tyr Glu Ala Gly Lys Arg Ala Ser Phe Met Gly Gly Ala
 50                  55                  60

Gly Ile Trp Ile Leu Ala Leu Ser Val Leu Met His Val Val Cys Ser
 65                  70                  75                  80

Gly Ile Ser Val Arg Ser Gly Ser Ala Lys Val Ala Phe Ser Ala Thr
                 85                  90                  95

Arg Ser Thr Asn His Glu Pro Ser Glu Met Ser Asn Arg Thr Met Thr
            100                 105                 110

Ile Tyr Phe Asp Gln Val Leu Val Asn Ile Gly Asn His Phe Asp Leu
            115                 120                 125

Ala Ser Ser Ile Phe Val Ala Pro Arg Lys Gly Ile Tyr Ser Phe Ser
130                 135                 140

Phe His Val Val Lys Val Tyr Asn Arg Gln Thr Ile Gln Val Ser Leu
145                 150                 155                 160

Met Gln Asn Gly Tyr Pro Val Ile Ser Ala Phe Ala Gly Asp Gln Asp
                165                 170                 175

Val Thr Arg Glu Ala Ala Ser Asn Gly Val Leu Leu Leu Met Glu Arg
            180                 185                 190

Glu Asp Lys Val His Leu Lys Leu Glu Arg Gly Asn Leu Met Gly Gly
            195                 200                 205

Trp Lys Tyr Ser Thr Phe Ser Gly Phe Leu Val Phe Pro Leu
            210                 215                 220

<210> SEQ ID NO 8
<211> LENGTH: 247
<212> TYPE: PRT
<213> ORGANISM: Homo sapiens

<400> SEQUENCE: 8

Met Leu Leu Leu Gln Ala Leu Leu Phe Leu Leu Ile Leu Pro Ser His
 1               5                   10                  15

Ala Glu Asp Asp Val Thr Thr Thr Glu Glu Leu Ala Pro Ala Leu Val
                 20                  25                  30

Pro Pro Pro Lys Gly Thr Cys Ala Gly Trp Met Ala Gly Ile Pro Gly
            35                  40                  45

His Pro Gly His Asn Gly Thr Pro Gly Arg Asp Gly Arg Asp Gly Thr
         50                  55                  60

Pro Gly Glu Lys Gly Glu Lys Gly Asp Ala Gly Leu Leu Gly Pro Lys
 65                  70                  75                  80

Gly Glu Thr Gly Asp Val Gly Met Thr Gly Ala Glu Gly Pro Arg Gly
                 85                  90                  95

Phe Pro Gln Thr Pro Gly Arg Lys Gly Glu Pro Gly Glu Ala Ala Tyr
            100                 105                 110

Met Tyr Arg Ser Ala Phe Ser Val Gly Leu Glu Thr Arg Val Thr Val
            115                 120                 125

Pro Asn Val Pro Ile Arg Phe Thr Lys Ile Phe Tyr Asn Gln Gln Asn
130                 135                 140

His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
                165                 170                 175

Ser Leu Phe Lys Lys Asp Lys Ala Val Leu Phe Thr Tyr Asp Gln Tyr

```
                     180              185              190
Gln Glu Lys Asn Val Asp Gln Ala Ser Gly Ser Val Leu Leu His Leu
            195                  200                  205
Glu Val Gly Asp Gln Val Trp Leu Gln Val Tyr Gly Asp Gly Asp His
        210                  215                  220
Asn Gly Leu Tyr Ala Asp Asn Val Asn Asp Ser Thr Phe Thr Gly Phe
225                  230                  235                  240
Leu Leu Tyr His Asp Thr Asn
                245

<210> SEQ ID NO 9
<211> LENGTH: 4517
<212> TYPE: DNA
<213> ORGANISM: Homo sapiens

<400> SEQUENCE: 9
ctgattccat accagagggg ctcaggatgc tgttgctggg agctgttcta ctgctattag     60
ctctgcccgg gcatgaccag gaaaccacga ctcaagggcc cggagtcctg cttccctgc    120 ccaagggggc ctgcacaggt tggatggcgg gcatcccagg gcatccgggc cataatgggg    180
ccccaggccg tgatggcaga gatggcaccc tggtgagaa gggtgagaaa ggagatccag    240
gtcttattgg tcctaaggga gacatcggtg aaaccggagt acccggggct gaaggtcccc    300
gaggctttcc gggaatccaa ggcaggaaag gagaacctgg agaaggtgcc tatgtatacc    360
gctcagcatt cagtgtggga ttggagactt acgttactat ccccaacatg cccattcgct    420
ttaccaagat cttctacaat cagcaaaacc actatgatgg ctccactggt aaattccact    480
gcaacattcc tgggctgtac tactttgcct accacatcac agtctatatg aaggatgtga    540
aggtcagcct cttcaagaag acaaggcta tgctcttcac ctatgatcag taccaggaaa    600
ataatgtgga ccaggcctcc ggctctgtgc tcctgcatct ggaggtgggc gaccaagtct    660
ggctccaggt gtatggggaa ggagagcgta atggactcta tgctgataat gacaatgact    720
ccaccttcac aggcttttctt ctctaccatg acaccaactg atcaccacta actcagagcc    780
tcctccaggc caaacagccc caaagtcaat taaaggcttt cagtacggtt aggaagttga    840
ttattattta gttggaggcc tttagatatt attcattcat ttactcattc atttattcat    900
tcattcatca agtaacttta aaaaaatcat atgctatgtt cccagtcctg gggagcttca    960
caaacatgac cagataactg actagaaaga agtagttgac agtgctattt tgtgcccact   1020
gtctctcctg atgctcatat caatcctata aggcacaggg aacaagcatt ctcctgtttt   1080
tacagattgt atcctgaggc tgagagagtt aagtgaatgt ctaaggtcac acagtattaa   1140
gtgacagtgc tagaaatcaa acccagagct gtggactttg ttcactagac tgtgcccttt   1200
tatagaggta catgttctct ttggagtgtt ggtaggtgtc tgtttcccac ctcacctgag   1260
agccattgaa tttgccttcc tcatgaatta aaacctcccc caagcagagc ttcctcagag   1320
aaagtggttc tatgatgaag tcctgtcttg gaaggactac tactcaatgg ccctgcact   1380 actctacttc ctcttaccta tgtcccttct catgcctttc cctccaacgg ggaaagccaa   1440
ctccatctct aagtgctgaa ctcatccctg ttcctcaagg ccacctggcc aggagcttct   1500
ctgatgtgat atccactttt ttttttttt gagatggagt ctcactctgt cacccaggct   1560
ggagtacagt gacacgacct cggctcactg cagcctcctt ctcctgggtc caagcaatta   1620
ttgtgcctca gcctcccgag tagctgagac ttcaggtgca ttcaccaca catggctaat   1680 ttttgtattt ttagtagaaa tggggtttcg tcatgttggc caggctggtc tcgaactcct   1740
```

-continued

| | | | | |
|---|---|---|---|---|
| ggcctaggtg | atccacccgc | ctcgacctcc | caaagtgctg | ggattacagg catgagccac | 1800 |
| catgcccagt | cgatatctca | cttttattt | tgccatggat | gagagtcctg ggtgtgagga | 1860 |
| acacctccca | ccaggctaga | ggcaactgcc | caggaaggac | tgtgcttccg tcacctctaa | 1920 |
| atcccttgca | gatccttgat | aaatgcctca | tgaagaccaa | tctcttgaat cccatatcta | 1980 |
| cccagaatta | actccattcc | agtctctgca | tgtaatcagt | tttatccaca gaaacatttt | 2040 |
| cattttagga | aatccctggt | ttaagtatca | atccttgttc | agctggacaa tatgaatctt | 2100 |
| ttccactgaa | gttagggatg | actgtgattt | tcagaacacg | tccagaattt ttcatcaaga | 2160 |
| aggtagcttg | agcctgaaat | gcaaaaccca | tggaggaatt | ctgaagccat tgtctccttg | 2220 |
| agtaccaaca | gggtcaggga | agactgggcc | tcctgaattt | attattgttc tttaagaatt | 2280 |
| acaggttgag | gtagttgatg | gtggtaaaca | ttctctcagg | agacaataac tccagtgatg | 2340 |
| tttttcaaag | attttagcaa | aaacagagta | aatagcattc | tctatcaata tataaattta | 2400 |
| aaaaactatc | tttttgctta | cagttttaaa | ttctgaacaa | tttctcttat atgtgtattg | 2460 |
| ctaatcatta | aggtattatt | ttttccacat | ataaagcttt | gtcttttgt tgttgttgtt | 2520 |
| gtttttaaga | tggagtttcc | ctctgttgcc | aggctagagt | gcagtggcat gatctcggct | 2580 |
| tactgcaacc | tttgcctccc | aggtttaagc | gattcttctg | cctcagcctc ccgagtagct | 2640 |
| gggaccacag | gtgcctacca | ccatgccagg | ctaattttg | tatttttagt aaagacaggg | 2700 |
| tttcaccata | ttggccaggc | tggtctcgaa | ctcctgacct | tgtgatctgc ccgcctccat | 2760 |
| tgtgttgtta | tttgtgagaa | agatagatat | gaggtttaga | gagggatgaa gaggtgagag | 2820 |
| taagccttgt | gttagtcaga | actctgtgtt | gtgaatgtca | ttcacaacag aaaacccaaa | 2880 |
| atattatgca | aactactgta | agcaagaaaa | ataaggaaa | aatggaaaca tttattcctt | 2940 |
| tgcataatag | aaattaccag | agttgttctg | tctttagata | aggtttgaac caaagctcaa | 3000 |
| aacaatcaag | acccttttct | gtatgtcctt | ctgttctgcc | ttccgcagtg taggctttac | 3060 |
| cctcaggtgc | tacacagtat | agttctaggg | tttccctccc | gatatcaaaa agactgtggc | 3120 |
| ctgcccagct | ctcgtatccc | caagccacac | catctggcta | aatggacatc atgttttctg | 3180 |
| gtgatgccca | agaggagag | aggaagctct | ctttcccaga | tgccccagca agtgtaacct | 3240 |
| tgcatctcat | tgctctggct | gagttgtgtg | cctgtttctg | accaatcact gagtcaggag | 3300 |
| gatgaaatat | tcatattgac | ttaattgcag | cttaagttag | gggtatgtag aggtatttc | 3360 |
| cctaaagcaa | aattgggaca | ctgttatcag | aaataggaga | gtggatgata gatgcaaaat | 3420 |
| aatacctgtc | cacaacaaac | tcttaatgct | gtgtttgagc | tttcatgagt ttcccagaga | 3480 |
| gacatagctg | gaaaattcct | attgattttc | tctaaaattt | caacaagtag ctaaagtctg | 3540 |
| gctatgctca | cagtctcaca | tctggtgggg | gtgggctcct | tacagaacac gctttcacag | 3600 |
| ttaccctaaa | ctctctgggg | cagggttatt | cctttgtgga | accagaggca cagagacagt | 3660 |
| caactgaggc | ccaacagagg | cctgagagaa | actgaggtca | agatttcagg attaatggtc | 3720 |
| ctgtgatgct | ttgaagtaca | attgtggatt | tgtccaattc | tctttagttc tgtcagcttt | 3780 |
| tgcttcatat | attttagcgc | tctattatta | gatatataca | tgtttagtat tatgtcttat | 3840 |
| tggtgcattt | actctcttat | cattatgtaa | tgtccttctt | tatctgtgat aattttctgt | 3900 |
| gttctgaagt | ctactttgtc | taaaaataac | atacgcactc | aacttccttt tctttcttcc | 3960 |
| ttccttctt | tcttccttcc | tttctttctc | tctctctctt | tccttccttc cttcctcctt | 4020 |
| ttctctctct | ctctctctct | ctctcttttc | ttgacagact | ctcgttctgt ggccctggct | 4080 |

-continued

```
ggagttcagt ggtgtgatct tggctcactg ctacctctac catgagcaat tctcctgcct      4140
cagcctccca agtagctgga actacaggct catgccactg cgcccagcta attttttgtat     4200 ttttcgtaga gacggggttt caccacattc gtcaggttgg tttcaaactc ctgactttgt      4260
gatccacccg cctcggcctc ccaaagtgct gggattacag gcatgagcca tcacacctgg      4320
tcaactttct ttttgattagt gttttttgtgg tatatctttt tccatcatgt tactttaaat   4380
atatctatat tattgtattt aaaatgtgtt tcttacagac tgcatgtagt tgggtataat      4440
ttttatccag tctaaaaata tctgtctttt aattggtgtt tagacaattt atatttaata     4500
aaatggtgga attaaa                                                     4517

<210> SEQ ID NO 10
<211> LENGTH: 729
<212> TYPE: DNA
<213> ORGANISM: Artificial Sequence
<220> FEATURE:
<223> OTHER INFORMATION: Degenerate nucleotide sequence encoding
      the zsig39 polypeptide of SEQ ID NO:2.

<400> SEQUENCE: 10
atgmgnccny tnytngtnyt nytnytnytn ggnytngcng cnggnwsncc nccnytngay       60
gayaayaara thccnwsnyt ntgyccnggn cayccnggny tnccnggnac nccnggncay      120
cayggnwsnc arggnytncc nggnmgngay ggnmgngayg gnmgngaygg ngcnccnggn      180
gcnccnggng araarggnga rggnggnmgn ccnggnytnc cnggnccnmg nggngayccn      240
ggnccnmgng gngargcngg nccngcnggn ccnacnggnc cngcnggnga rtgywsngtn      300
ccnccnmgnw sngcnttyws ngcnaarmgn wsngarwsnm gngtnccncc nccnwsngay      360
gcnccnytnc cnttygaymg ngtnytngtn aaygarcarg gncaytayga ygcngtnacn      420
ggnaarttya cntgycargt nccnggngtn taytayttyg cngtncaygc nacngtntay      480
mgngcnwsny tncarttyga yytngtnaar aayggngarw snathgcnws nttyttycar      540
ttyttyggng gntggccnaa rccngcnwsn ytnwsnggng gngcnatggt nmgnytngar      600
ccngargayc argtntgggt ncargtnggn gtnggngayt ayathggnat htaygcnwsn      660
athaaracng aywsnacntt ywsnggntty ytngtntayw sngaytggca ywsnwsnccn      720 gtnttygcn                                                             729

<210> SEQ ID NO 11
<211> LENGTH: 17
<212> TYPE: DNA
<213> ORGANISM: Artificial Sequence
<220> FEATURE:
<223> OTHER INFORMATION: Oligonucleotide ZC447

<400> SEQUENCE: 11
taacaatttc acacagg                                                     17

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide ZC976

<400> SEQUENCE: 12
cgttgtaaaa cgacggcc                                                    18

<210> SEQ ID NO 13
```

```
<211> LENGTH: 20
<212> TYPE: DNA
<213> ORGANISM: Artificial Sequence
<220> FEATURE:
<223> OTHER INFORMATION: Oligonucleotide ZC14707

<400> SEQUENCE: 13
cccactggac gacaacaaga                                               20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide ZC14708

<400> SEQUENCE: 14
agcacactcc tctggtcttg                                               20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide ZC14760

<400> SEQUENCE: 15
ccaatgtagt cacccacacc                                               20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide ZC14758

<400> SEQUENCE: 16
tggtgaacga gcagggacat                                               20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide ZC14759

<400> SEQUENCE: 17
tccccagtct ttgcttagtg                                               20

<210> SEQ ID NO 18
<211> LENGTH: 18
<212> TYPE: DNA
<213> ORGANISM: Artificial Sequence
<220> FEATURE:
<223> OTHER INFORMATION: Oligonucleotide ZC15002

<400> SEQUENCE: 18
agggaggtgg ggtagagc                                                 18

<210> SEQ ID NO 19
<211> LENGTH: 18
<212> TYPE: DNA
<213> ORGANISM: Artificial Sequence
<220> FEATURE:
<223> OTHER INFORMATION: Oligonucleotide ZC 15003

<400> SEQUENCE: 19
```

```
tggggggactt acacttgc                                              18
```

<210> SEQ ID NO 20
<211> LENGTH: 6
<212> TYPE: PRT
<213> ORGANISM: Artificial Sequence
<220> FEATURE:
<223> OTHER INFORMATION: Glu-Glu affinity tag peptide

<400> SEQUENCE: 20

Glu Tyr Met Pro Val Asp
 1               5

<210> SEQ ID NO 21
<211> LENGTH: 26
<212> TYPE: DNA
<213> ORGANISM: Artificial Sequence
<220> FEATURE:
<223> OTHER INFORMATION: Oligonucleotide ZC15037

<400> SEQUENCE: 21

```
actcattcta gactacagca aagact                                       26
```

<210> SEQ ID NO 22
<211> LENGTH: 25
<212> TYPE: DNA
<213> ORGANISM: Artificial Sequence
<220> FEATURE:
<223> OTHER INFORMATION: Oligonucleotide ZC15038

<400> SEQUENCE: 22

```
atgtatggat ccctggacga caaca                                        25
```

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide ZC13006

<400> SEQUENCE: 23

```
ggctgtcctc taagcgtcac                                              20
```

<210> SEQ ID NO 24
<211> LENGTH: 19
<212> TYPE: DNA
<213> ORGANISM: Artificial Sequence
<220> FEATURE:
<223> OTHER INFORMATION: Oligonucleotide ZC13007

<400> SEQUENCE: 24

```
aggggtcaca gggatgcca                                               19
```

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide ZC15609

<400> SEQUENCE: 25

```
ttgtgagaat tcatgaggcc actc                                         24
```

<210> SEQ ID NO 26
<211> LENGTH: 25

<212> TYPE: DNA
<213> ORGANISM: Oligonucleotide ZCArtificial Sequence
<220> FEATURE:
<223> OTHER INFORMATION: Oligonucleotide ZC15232

<400> SEQUENCE: 26
attcaaggat ccagcaaaga caggt                                              25

<210> SEQ ID NO 27
<211> LENGTH:
<212> TYPE:
<211> LENGTH:
<212> TYPE:
<213> ORGANISM:

<400> SEQUENCE: 27

This Sequence is intentionally skipped

<210> SEQ ID NO 28
<211> LENGTH: 144
<212> TYPE: DNA
<213> ORGANISM: Artificial Sequence
<220> FEATURE:
<223> OTHER INFORMATION: N-terminal untagged linker

<400> SEQUENCE: 28
ttattgttta tcaatactac tattgctagc attgctgcta agaagaagg tgtaagcttg         60 gacaagagag aactggacga caacaagatc cccagcctct gcccggggca ccccggcctt       120
ccaggcacgc cgggccacca tggc                                              144

<210> SEQ ID NO 29
<211> LENGTH: 144
<212> TYPE: DNA
<213> ORGANISM: Artificial Sequence
<220> FEATURE:
<223> OTHER INFORMATION: N-terminal Glu-Glu tag linker

<400> SEQUENCE: 29
agcattgctg ctaaagaaga aggtgtaagc ttggacaaga gagaagaaga atacatgcca        60
atggaaggtg gtctggacga caacaagatc cccagcctct gcccggggca ccccggcctt      120
ccaggcacgc cgggccacca tggc                                              144

<210> SEQ ID NO 30
<211> LENGTH: 147
<212> TYPE: DNA
<213> ORGANISM: Artificial Sequence
<220> FEATURE:
<223> OTHER INFORMATION: C-terminal untagged linker

<400> SEQUENCE: 30
agcatcaaga cagacagcag gttctccgga tttctggtgt actccgactg gcacagctcc        60
ccagtctttg cttagatttc ggctgcctgt ttggatattt ttataatttt tgagagtttg      120
ccaactaatg tttttctctt ctatgat                                           147

<210> SEQ ID NO 31
<211> LENGTH: 144
<212> TYPE: DNA
<213> ORGANISM: Artificial Sequence
<220> FEATURE:
<223> OTHER INFORMATION: C-terminal Glu-Glu tag linker

<400> SEQUENCE: 31

```
agcatcaaga cagacagcac cttctccgga tttctggtgt actccgactg gcacagctcc        60
ccagtctttg ctggagggga ggagtatatg cctatggagt agaattccta gtattctagg       120
gctgcctgtt tggatatttt tata                                              144

<210> SEQ ID NO 32
<211> LENGTH: 51
<212> TYPE: DNA
<213> ORGANISM: Artificial Sequence
<220> FEATURE:
<223> OTHER INFORMATION: Oligonucleotide ZC13731

<400> SEQUENCE: 32
ggtgtaagct tggacaagag agaagaagaa tacatgccaa tggaaggtgg t                 51

<210> SEQ ID NO 33
<211> LENGTH: 62
<212> TYPE: DNA
<213> ORGANISM: Oligonucleotide ZCArtificial Sequence
<220> FEATURE:
<223> OTHER INFORMATION: Oligonucleotide ZC15268

<400> SEQUENCE: 33
tgccccgggc agaggctggg gatcttgttg tcgtccagac caccttccat tggcatgtat        60
tc                                                                       62

<210> SEQ ID NO 34
<211> LENGTH: 44
<212> TYPE: DNA
<213> ORGANISM: Artificial Sequence
<220> FEATURE:
<223> OTHER INFORMATION: Oligonucleotide ZC13487

<400> SEQUENCE: 34
agcattgctg ctaaagaaga aggtgtaagc ttggacaaga gaga                         44

<210> SEQ ID NO 35
<211> LENGTH: 51
<212> TYPE: DNA
<213> ORGANISM: Artificial Sequence
<220> FEATURE:
<223> OTHER INFORMATION: Oligonucleotide ZC15273

<400> SEQUENCE: 35
catggtggcc cggcgtgcct ggaaggccgg ggtgccccgg cagaggctg g                  51

<210> SEQ ID NO 36
<211> LENGTH: 50
<212> TYPE: DNA
<213> ORGANISM: Artificial Sequence
<220> FEATURE:
<223> OTHER INFORMATION: Oligonucleotide ZC15273

<400> SEQUENCE: 36
catcaagaca gacagcacct tctccggatt tctggtgtac tccgactggc                   50

<210> SEQ ID NO 37
<211> LENGTH: 65
<212> TYPE: DNA
<213> ORGANISM: Artificial Sequence
<220> FEATURE:
<223> OTHER INFORMATION: Oligonucleotide ZC15724

<400> SEQUENCE: 37
tttctggtgt actccgactg gcacagctcc ccagtctttg cttagaattc ggctgcctgt        60
``` ttgga                                                               65

<210> SEQ ID NO 38
<211> LENGTH: 63
<212> TYPE: DNA
<213> ORGANISM: Artificial Sequence
<220> FEATURE:
<223> OTHER INFORMATION: Oligonucleotide ZC15223

<400> SEQUENCE: 38
tggcaaactc tcaaaaatta taaaaatatc caaacaggca gccctagaat actaggaatt    60
cta                                                                 63

<210> SEQ ID NO 39
<211> LENGTH: 52
<212> TYPE: DNA
<213> ORGANISM: Artificial Sequence
<220> FEATURE:
<223> OTHER INFORMATION: Oligonucleotide ZC13734

<400> SEQUENCE: 39
atcatagaag agaaaaacat tagttggcaa actctcaaaa attataaaaa ta            52

<210> SEQ ID NO 40
<211> LENGTH: 40
<212> TYPE: DNA
<213> ORGANISM: Artificial Sequence
<220> FEATURE:
<223> OTHER INFORMATION: Oligonucleotide ZC14822

<400> SEQUENCE: 40
acggtttatt gtttatcaat actactattg ctagcattgc                         40

<210> SEQ ID NO 41
<211> LENGTH: 62
<212> TYPE: DNA
<213> ORGANISM: Artificial Sequence
<220> FEATURE:
<223> OTHER INFORMATION: Oligonucleotide ZC14821

<400> SEQUENCE: 41
tcaatactac tattgctagc attgctgcta agaagaagg tgtaagcttg gacaagagag     60
aa                                                                  62

<210> SEQ ID NO 42
<211> LENGTH: 63
<212> TYPE: DNA
<213> ORGANISM: Artificial Sequence
<220> FEATURE:
<223> OTHER INFORMATION: Oligonucleotide ZC15269

<400> SEQUENCE: 42
tgccccgggc agaggctggg gatcttgttg tcgtccagtt ctctcttgtc caagcttaca    60
cct                                                                 63

<210> SEQ ID NO 43
<211> LENGTH: 51
<212> TYPE: DNA
<213> ORGANISM: Artificial Sequence
<220> FEATURE:
<223> OTHER INFORMATION: Oligonucleotide ZC15274

<400> SEQUENCE: 43

```
catggtggcc cggcgtgcct ggaaggccgg ggtgccccgg gcagaggctg g         51
```

<210> SEQ ID NO 44
<211> LENGTH: 50
<212> TYPE: DNA
<213> ORGANISM: Artificial Sequence
<220> FEATURE:
<223> OTHER INFORMATION: Oligonucleotide ZC15273

<400> SEQUENCE: 44

```
catcaagaca gacagcacct tctccggatt tctggtgtac tccgactggc           50
```

<210> SEQ ID NO 45
<211> LENGTH: 68
<212> TYPE: DNA
<213> ORGANISM: Artificial Sequence
<220> FEATURE:
<223> OTHER INFORMATION: Oligonucleotide ZC15267

<400> SEQUENCE: 45

```
atttctggtg tactccgact ggcacagctc cccagtcttt gctggtggtg aagaatacat    60
gccaatgg                                                             68
```

<210> SEQ ID NO 46
<211> LENGTH: 58
<212> TYPE: DNA
<213> ORGANISM: Artificial Sequence
<220> FEATURE:
<223> OTHER INFORMATION: Oligonucleotide ZC14819

<400> SEQUENCE: 46

```
aacaggcagc cctagaatac taggaattct attccattgg catgtattct tcaccacc       58
```

<210> SEQ ID NO 47
<211> LENGTH: 39
<212> TYPE: DNA
<213> ORGANISM: Artificial Sequence
<220> FEATURE:
<223> OTHER INFORMATION: Oligonucleotide ZC14820

<400> SEQUENCE: 47

```
attataaaaa tatccaaaca ggcagcccta gaatactag                           39
```